United States Patent
Umemoto et al.

(10) Patent No.: US 8,653,254 B2
(45) Date of Patent: Feb. 18, 2014

(54) PROCESS FOR PRODUCING NUCLEOSIDE

(75) Inventors: Tadashi Umemoto, Kanagawa (JP); Yoji Hayase, Kanagawa (JP); Shumpei Murata, Kanagawa (JP); Kenichi Miyata, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 149 days.

(21) Appl. No.: 13/260,096

(22) PCT Filed: Mar. 30, 2010

(86) PCT No.: PCT/JP2010/055670
§ 371 (c)(1),
(2), (4) Date: Dec. 6, 2011

(87) PCT Pub. No.: WO2010/113937
PCT Pub. Date: Oct. 7, 2010

(65) Prior Publication Data
US 2012/0071646 A1 Mar. 22, 2012

(30) Foreign Application Priority Data
Mar. 31, 2009 (JP) .................................. 2009-085897

(51) Int. Cl.
*C07H 21/00* (2006.01)

(52) U.S. Cl.
USPC ........................................ 536/25.3; 536/25.31

(58) Field of Classification Search
None
See application file for complete search history.

(56) References Cited

U.S. PATENT DOCUMENTS

| 5,962,675 | A | 10/1999 | Beigelman et al. |
| 7,427,672 | B2 | 9/2008 | Imanishi et al. |
| 2007/0167387 | A1 | 7/2007 | Imanishi et al. |

FOREIGN PATENT DOCUMENTS

| WO | WO 2005/021570 A1 | 3/2005 |
| WO | WO 2010/021344 A1 | 2/2010 |

OTHER PUBLICATIONS

English-language International Search Report from the Japanese Patent Office for International Application No. PCT/JP2010/055670, mailing date Jun. 1, 2010.
Beigelman et al.; "Improved Synthetic Approaches Toward 2'-O-Methyl-Adenosine and Guanosine and Their N-Acyl Derivatives", Tetrahedron vol. 56, pp. 1047-1056, (2000).
Imazawa et al.; "Facile Synthesis of 2'-Amino-2'-Deoxyribofuranosyl Purines", J. Org. Chem., vol. 44, No. 12, pp. 2039-2041, (1979).
Mitsuoka et al.; "Synthesis of 2',4'-BNA$^{COC}$ Bearing a Purine Nucleobase", Nucleic Acids Symposium Series, No. 50, pp. 13-14, (2006).
Li et al.; "Synthesis of 2'-Deoxy-2'-C-α-Methylpurine Nucleosides", Synthesis, No. 17, pp. 2865-2870, (2005).
Ravn et al.; "Synthesis of 2'-Amino-LNA Purine Nucleosides", Nucleosides, Nucleotides, and Nucleic Acids, vol. 25, pp. 843-847, (2006).
Zou et al.; "High-Yield Regioselective Synthesis of 9-Glycosyl Guanine Nucleosides and Analogues Via Coupling With 2-N-Acetyl-6-O-Diphenylcarbamoylguanine", Can. J. Chem., 65, Communications, pp. 1436-1437, (1987).
Takuma et al.; "Synthesis and Properties of 2',4'-BNA$^{NC}$ Bearing an Adenine Nucleobase", Nucleic Acids at the Chemistry-Biology Interface 07 & 08 Sep. 2009, cover sheet and p. 80, (2009).
Takuma et al.; "Synthesis and Functional Assessment of 2',4'-BNA$^{NC}$ Analogue Incorporating Purine Base", 59$^{th}$ General Meeting/Mass Meeting of Pharmaceutical Society of Japan, Kinki Branch, 5 pages, (2009).

*Primary Examiner* — Patrick Lewis
(74) *Attorney, Agent, or Firm* — Finnegan, Henderson, Farabow, Garrett & Dunner LLP

(57) ABSTRACT

There is a demand for a convenient production method of an NC type purine nucleoside.
The present invention relates to a method of producing a purine nucleoside represented the formula (I')

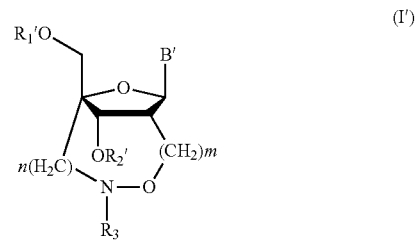

or a salt thereof, which comprising reacting a pyrimidine nucleoside represented by the formula (I)

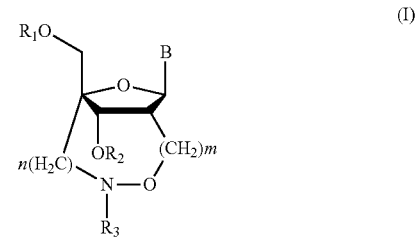

or a salt thereof with a purine nucleobase represented by the formula B'H in the presence of a Lewis acid.

22 Claims, No Drawings

PROCESS FOR PRODUCING NUCLEOSIDE

TECHNICAL FIELD

The present invention relates to a production method of a nucleoside. Particularly, the present invention relates to a production method of a nucleoside analog which is an intermediate for producing a stable oligonucleotide analog having a superior antisense, antigene and RNA interference (RNAi) activity.

BACKGROUND OF THE INVENTION

In 1978, an antisense oligonucleotide (antisense molecule) was first reported to have inhibited influenza virus infection. Thereafter, it has also been reported to have inhibited expression of cancer gene and AIDS infection. Since antisense oligonucleotide specifically regulates expression of undesirable genes, the field thereof is one of the most expected fields in recent years as a target of a pharmaceutical product development.

However, when natural DNA or RNA oligonucleotide is applied as an antisense molecule to this method, many problems occur such as hydrolysis by enzymes in the body, not high cellular membrane permeability and the like. To solve such problems, many nucleic acid derivatives have been synthesized, and the properties thereof have been studied. For example, phosphorothioates wherein an oxygen atom on the phosphorus atom of nucleic acid is substituted by a sulfur atom, and methylphosphonates wherein an oxygen atom on the phosphorus atom of nucleic acid is substituted by a methyl group have been synthesized, and recently, a molecule wherein a phosphorus atom is also substituted by a carbon atom, and a molecule wherein ribose is modified to an acyclic skeleton have also been synthesized.

Recently, it has been reported that a DNA or RNA oligonucleotide containing an artificial nucleic acid 2',4'BNA$^{NC}$ unit represented by the formula

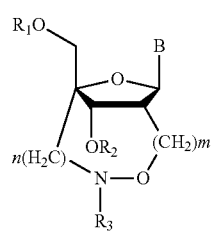

wherein each symbol is as defined in patent document 1, and the carbon atom at the 2-position and the carbon atom at the 4-position of the sugar moiety in the nucleoside molecule are NO-bridged (in the present specification, such compound is sometimes generically referred to as "NC type nucleoside") is a highly useful oligonucleotide derivative, since it shows a very high ability to form a double strand of complementary RNA chain, is superior in nuclease resistance, and permits binding of various other functional molecules to the NO bond (see patent document 1).

Non-patent document 1 discloses production methods of 2',4'-BNA$^{COC}$ units having a purine nucleobase (to be referred to as "COC type (purine) nucleoside" in the present specification).

Non-patent document 2 discloses a glycosylation reaction using a silylated purine nucleobase.

Non-patent document 3 discloses synthetic methods of amino LNA purine derivatives.

Non-patent document 4 discloses synthetic methods of 2'-amino-2'-deoxynucleoside purine derivatives.

Non-patent document 5 and patent document 2 disclose synthetic methods of 2'-O-Me-nucleosidepurine derivatives.

However, none of the above-mentioned documents disclose a method of directly synthesizing an NC type purine nucleoside from an NC type pyrimidine nucleoside.

DOCUMENT LIST

Patent Document

Patent Document 1: WO 2005/021570
Patent Document 2: U.S. Pat. No. 5,962,675

Non-Patent Document

Non-Patent Document 1: Mitsuoka Y. et al., Nucleic Acids Symposium Series, No. 50, pp. 13-14
Non-Patent Document 2: Synthesis 2005, No. 17, 2865-2870
Non-Patent Document 3: Nucleosides, Nucleotides & Nucleic Acids, Volume 25, Number 8, 2006, pp. 843-847 (5)
Non-Patent Document 4: J. Org. Chem., Vol. 44, No. 12, 1979, pp. 2039
Non-Patent Document 5: Tetrahedron 56 (2000), pp. 1047-1056

SUMMARY OF THE INVENTION

Problems to be Solved by the Invention

There is a demand for a convenient and easy production method of an NC type purine nucleoside having a purine nucleobase directly from an NC type pyrimidine nucleoside.

Means of Solving the Problems

The present inventors have found for the first time that an NC type purine nucleoside can be produced by reacting an NC type pyrimidine nucleoside with a purine nucleobase in the presence of a Lewis acid.

Based on these findings, the present inventors have further conducted intensive studies and completed the present invention.

Accordingly, the present invention relates to

[1] a method of producing a purine nucleoside represented by the formula (I')

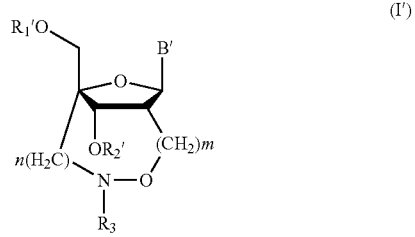

(hereinafter to be referred to as compound (I')) or a salt thereof, which comprises reacting a pyrimidine nucleoside represented by the formula (I)

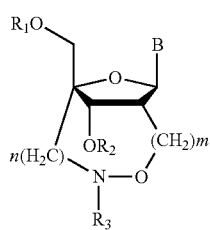

(hereinafter to be referred to as compound (I)) or a salt thereof with a purine nucleobase represented by the formula B'H in a solvent, in the presence of a Lewis acid:
wherein
$R_1$ and $R_1'$ are each independently a hydrogen atom, a hydroxy-protecting group, an alkyl group, an alkenyl group, a cycloalkyl group, an aryl group optionally having substituent(s), an aralkyl group optionally having substituent(s), an acyl group, an aliphatic or aromatic sulfonyl group or a silyl group,
$R_2$ and $R_2'$ are each independently a hydrogen atom, a hydroxy-protecting group, an alkyl group, an alkenyl group, a cycloalkyl group, an aryl group optionally having substituent(s), an aralkyl group optionally having substituent(s), an acyl group, an aliphatic or aromatic sulfonyl group or a silyl group, or
$R_1$ and $R_2$ in combination or $R_1'$ and $R_2'$ in combination optionally form a group represented by the formula

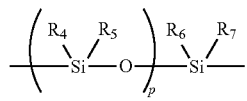

wherein
$R_4$ in the number of p, $R_5$ in the number of p, $R_6$ and $R_7$ are each independently an alkyl group or an aryl group, and
p is an integer of 1 to 3,
$R_3$ is a hydrogen atom, an alkyl group, an alkenyl group, a cycloalkyl group, an aryl group optionally having substituent(s), an aralkyl group optionally having substituent(s), an acyl group, an aliphatic or aromatic sulfonyl group or a functional molecular unit substituent,
B is a residue derived from a pyrimidine nucleobase optionally having substituent(s),
B' is a residue derived from a purine nucleobase optionally having substituent(s),
m is an integer of 0 to 2, and
n is an integer of 1 to 3;
[2] the method of [1], wherein B is a residue derived from a pyrimidine nucleobase optionally having substituent(s), and is bonded at the N1-position on the pyrimidine ring, and B' is a residue derived from a purine nucleobase optionally having substituent(s), and is bonded at the N9-position on the purine ring;
[3] the method of [1] or [2], wherein B is a residue derived from a pyrimidine nucleobase protected by an amino-protecting group, and is bonded at the N1-position on the pyrimidine ring;
[4] the method of [1] or [2], wherein B is a residue derived from a thymine nucleobase wherein the nitrogen atom at the N3-position is protected by a benzoyl group, which is bonded at the N1-position on the pyrimidine ring;
[5] the method of any of [1] to [4], wherein B' is a residue derived from a purine nucleobase having a bulky substituent at the C6-position on the purine ring and optionally having additional substituent(s), and is bonded at the N9-position on the purine ring;
[6] the method of any of [1] to [4], wherein B' is a residue derived from a purine nucleobase having an amino group optionally protected by a benzoyl group at the C6-position, and is bonded at the N9-position on the purine ring;
[7] the method of any of [1] to [4], wherein B' is a residue derived from a purine nucleobase having a hydroxyl group optionally protected by a diphenylcarbamoyl group at the C6-position, and optionally having an amino group protected by an amino-protecting group, and is bonded at the N9-position on the purine ring;
[8] the method of any of [1] to [4], wherein B' is a residue derived from a purine nucleobase having an oxo group at the C6-position, and optionally having an amino group protected by an amino-protecting group, and is bonded at the N9-position on the purine ring;
[9] the method of any of [1] to [8], wherein the reaction is performed in the presence of a silylating agent;
[10] the method of any of [1] to [9], wherein the reaction is performed at 80 to 120° C.;
[11] the method of any of [1] to [10], wherein the solvent is toluene;
[12] the method of any of [1] to [11], wherein the reaction is performed by reacting the pyrimidine nucleoside represented by the formula (I)

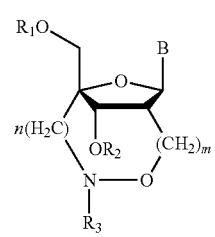

wherein each symbol is as defined in [1], or a salt thereof, with the purine nucleobase represented by the formula B'H wherein B' is as defined in [1], in the presence of the Lewis acid and a silylating agent, and then subjecting the resulting compound to a reaction for removal of a silyl group derived from the silylating agent;
[13] the method of any of [1] to [12], wherein $R_1$ and $R_1'$ are each independently a hydrogen atom; an acyl group; an aliphatic or aromatic sulfonyl group; a methyl group substituted by 1 to 3 aryl groups; a methyl group substituted by 1 to 3 aryl groups optionally substituted by 1 to 3 substituents selected from the group consisting of alkyl, alkoxy, a halogen atom and cyano; or a silyl group;
[14] the method of any of [1] to [12], wherein $R_1$ and $R_1'$ are each independently a hydrogen atom, an acetyl group, a benzoyl group, a methanesulfonyl group, a p-toluenesulfonyl group, a benzyl group, a p-methoxybenzyl group or a tert-butyldiphenylsilyl group;
[15] the method of any of [1] to [14], wherein $R_2$ and $R_2'$ are each independently a hydrogen atom; an acyl group; an aliphatic or aromatic sulfonyl group; a methyl group substituted by 1 to 3 aryl groups; a methyl group substituted by 1 to 3 aryl groups optionally substituted by 1 to 3 substituents selected from the group consisting of alkyl, alkoxy, a halogen atom and cyano; or a silyl group;

[16] the method of any of [1] to [14], wherein $R_2$ and $R_2'$ are each independently a hydrogen atom, an acetyl group, a benzoyl group, a methanesulfonyl group, a p-toluenesulfonyl group, a benzyl group, a p-methoxybenzyl group or a tert-butyldiphenylsilyl group;

[17] the method of any of [1] to [12], wherein $R_1$ and $R_2$ in combination or $R_1'$ and $R_2'$ in combination form a group represented by the formula

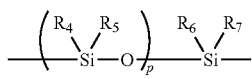

wherein
$R_4$ in the number of p, $R_5$ in the number of p, $R_6$ and $R_7$ are each independently a $C_{1-6}$ alkyl group, and
p is an integer of 1 to 3;

[18] the method of any of [1] to [17], wherein $R_3$ is a hydrogen atom, an alkyl group, an alkenyl group, an aryl group, a methyl group substituted by 1 to 3 aryl groups, an aliphatic or aromatic sulfonyl group, a phenoxyacetyl group or a functional molecular unit substituent;

[19] the method of any of [1] to [17], wherein $R_3$ is a $C_{1-6}$ alkyl group;

[20] the method of any of [1] to [19], wherein the functional molecular unit substituent is a residue derived from a fluorescence·luminescence-labeling molecule, a residue derived from a chemiluminescence-labeling molecule, a residue derived from a molecule with nucleic acid-cleavage activity, a residue derived from a intracellular transport signal peptide, or a residue derived from a nuclear localization signal peptide;

[21] the method of any of [1] to [20], wherein m is 0 and n is 1;

[22] the method of any of [1] to [4] and [9] to [21], wherein B' is a residue derived from a purine nucleobase optionally having substituent(s), and is bonded at the N9-position on the purine ring;

[23] a method of producing compound (I') or a salt thereof, comprising reacting compound (I) or a salt thereof with a purine nucleobase wherein the dissociative hydrogen atom is silylated, which is represented by the formula B'H wherein B' is as defined in [1], in a solvent, in the presence of a Lewis acid.

Effect of the Invention

According to the present invention, an NC type purine nucleotide can be produced conveniently with ease. In addition, since the purine nucleobase moiety can be N9 position-selectively transglycosylated, an NC type purine nucleoside can be regioselectively produced.

DETAILED DESCRIPTION OF THE INVENTION

The present invention provides a "method of producing compound (I') or a salt thereof, which comprising reacting compound (I) or a salt thereof with a purine nucleobase represented by the formula B'H wherein B' is a residue derived from a purine nucleobase optionally having substituent(s), in a solvent, in the presence of a Lewis acid".

In the present specification, examples of the "halogen atom" include fluorine atom, chlorine atom, bromine atom and iodine atom.

In the present specification, examples of the "alkyl (group)" include linear or branched chain alkyl (group) having 1 to 6 carbon atoms such as methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl, and linear or branched chain alkyl (group) having 7 to 20 carbon atoms such as heptyl, octyl, nonyl, decyl and the like. The "alkyl (group)" is preferably linear or branched chain alkyl (group) having 1 to 6 carbon atoms.

In the present specification, examples of the "alkenyl (group)" include linear or branched chain alkenyl (group) having 2 to 6 carbon atoms such as ethenyl(vinyl), 1-propenyl, 2-propenyl(allyl), 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl and 5-hexenyl, and geranyl, farnesyl and the like. The "alkenyl (group)" is preferably linear or branched chain alkenyl (group) having 2 to 6 carbon atoms.

In the present specification, examples of the "cycloalkyl group" include cycloalkyl groups having 3 to 10 carbon atoms such as cyclopropyl, cyclobutyl, cyclopentyl, cyclohexyl, cycloheptyl, cyclooctyl, norbornyl, adamantyl and the like. The "cycloalkyl group" is preferably a cycloalkyl group having 3 to 8 carbon atoms such as cyclopropyl, cyclobutyl, cyclopentyl, cyclohexyl, cycloheptyl, cyclooctyl and the like.

In the present specification, examples of the "alkoxy (group)" include linear or branched chain alkoxy (group) having 1 to 6 carbon atoms such as methoxy, ethoxy, n-propoxy, isopropoxy, n-butoxy, isobutoxy, sec-butoxy, tert-butoxy, n-pentyloxy, isopentyloxy, 2-methylbutyloxy, neopentyloxy, 1-ethylpropyloxy, n-hexyloxy, isohexyloxy, 4-methylpentyloxy, 3-methylpentyloxy, 2-methylpentyloxy, 1-methylpentyloxy, 3,3-dimethylbutyloxy, 2,2-dimethylbutyloxy, 1,1-dimethylbutyloxy, 1,2-dimethylbutyloxy, 1,3-dimethylbutyloxy, 2,3-dimethylbutyloxy and 2-ethylbutyloxy.

In the present specification, examples of the "aryl (group)" include aryl (group) having 6 to 14 carbon atoms such as phenyl, naphthyl, phenanthrenyl, anthracenyl and the like.

In the present specification, examples of the substituent for the "aryl group optionally having substituent(s)" include groups selected from a halogen atom, alkyl, a hydroxyl group, alkoxy, aryloxy, amino, nitro, trifluoromethyl and phenyl. The number of the substituents is 1 to 4, preferably 1 to 3. Examples of the aryl group optionally having substituent(s) include 2-methylphenyl, 4-methylphenyl, 2,6-dimethylphenyl, 2-chlorophenyl, 4-chlorophenyl, 2,4-dichlorophenyl, 2,5-dichlorophenyl, 2-bromophenyl, 4-methoxyphenyl, 4-chloro-2-nitrophenyl, 4-nitrophenyl, 2,4-dinitrophenyl and biphenyl.

In the present specification, examples of the "aralkyl (group)" include alkyl (group) having 1 to 6 carbon atoms which is substituted by aryl group(s) such as a "methyl group substituted by 1 to 3 aryl groups" (e.g. benzyl, α-naphthylmethyl, β-naphthylmethyl, phenanthrenylmethyl, anthracenylmethyl, diphenylmethyl, triphenylmethyl(trityl), α-naphthyldiphenylmethyl, 9-anthrylmethyl), and "alkyl (group) having 2 to 6 carbon atoms which is substituted by aryl group(s)" (e.g., 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-phenylhexyl, 2-phenylhexyl, 3-phenylhexyl, 4-phenylhexyl, 5-phenylhexyl, 6-phenylhexyl, 1-naphthylpentyl, 2-naphthylpentyl, 3-naphthylpentyl, 4-naphthylpentyl, 5-naphthylpentyl, 6-naphthylpentyl), and the like.

In the present specification, examples of the substituent for the "aralkyl group optionally having substituent(s)" include groups selected from alkyl, alkoxy, a halogen atom, cyano and nitro. The number of the substituents is 1 to 3. Preferable examples of the "aralkyl group optionally having substituent(s)" include a "methyl group substituted by 1 to 3 aryl groups", and a "methyl group substituted by 1 to 3 aryl groups optionally substituted by 1 to 3 substituents selected from alkyl, alkoxy, a halogen atom, cyano and nitro" (e.g., 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 2-nitrobenzyl, 4-nitrobenzyl, 4-chlorobenzyl, 4-bromobenzyl, 4-cyanobenzyl), and more preferable examples thereof include 4-methoxyphenyldiphenylmethyl and 4,4'-dimethoxytriphenylmethyl.

In the present specification, examples of the "acyl group" include
(a) an "aliphatic acyl group" such as
(i) an alkylcarbonyl group such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl and heneicosanoyl,
(ii) a carboxyalkylcarbonyl group such as succinoyl, glutaroyl and adipoyl,
(iii) a haloalkylcarbonyl group such as chloroacetyl, dichloroacetyl, trichloroacetyl and trifluoroacetyl,
(iv) an alkoxyalkylcarbonyl group such as methoxyacetyl,
(v) an aryloxyalkylcarbonyl group such as phenoxyacetyl,
(vi) an alkenylcarbonyl group such as (E)-2-methyl-2-butenoyl, and
(vii) a mono- or di-alkylcarbamoyl group such as monomethylcarbamoyl, dimethylcarbamoyl, monoethylcarbamoyl and diethylcarbamoyl; and
(b) an "aromatic acyl group" such as
(i) an arylcarbonyl group such as benzoyl, α-naphthoyl and β-naphthoyl; a haloarylcarbonyl group such as 2-bromobenzoyl and 4-chlorobenzoyl,
(ii) an alkyl-substituted arylcarbonyl group such as 2,4,6-trimethylbenzoyl and 4-toluoyl; an alkoxy-substituted arylcarbonyl group such as 4-anisoyl(p-methoxybenzoyl),
(iii) a carboxy-substituted arylcarbonyl group such as 2-carboxybenzoyl, 3-carboxybenzoyl and 4-carboxybenzoyl,
(iv) a nitro-substituted arylcarbonyl group such as 4-nitrobenzoyl and 2-nitrobenzoyl,
(v) an alkoxycarbonyl-substituted arylcarbonyl group such as 2-(methoxycarbonyl)benzoyl,
(vi) an aryl-substituted arylcarbonyl group such as 4-phenylbenzoyl, and
(vii) a mono- or di-arylcarbamoyl group such as monophenylcarbamoyl and diphenylcarbamoyl, and the "acyl group" is preferably formyl, acetyl, propionyl, butyryl, isobutyryl, pentanoyl, pivaloyl, benzoyl or phenoxyacetyl.

In the present specification, examples of the "aliphatic sulfonyl group" include sulfonyl groups substituted by linear or branched chain alkyl group(s) having 1 to 6 carbon atoms, such as methanesulfonyl and ethanesulfonyl.

Examples of the "aromatic sulfonyl group" include sulfonyl groups substituted by an "aryl group optionally having substituent(s)", such as benzenesulfonyl and p-toluenesulfonyl. The substituent for the aryl group is particularly preferably a alkyl group having 1 to 6 carbon atoms such as methyl, ethyl and the like.

The "aliphatic or aromatic sulfonyl group" is preferably a methanesulfonyl group or a p-toluenesulfonyl group.

In the present specification, examples of the "silyl group" include
(i) a trialkylsilyl group such as trimethylsilyl, triethylsilyl, isopropyldimethylsilyl, tert-butyldimethylsilyl, methyldiisopropylsilyl, methyldi-t-butylsilyl and triisopropylsilyl,
(ii) a diarylalkylsilyl group and a dialkylarylsilyl group, each of which is substituted by an alkyl group and an aryl group, such as diphenylmethylsilyl, diphenylbutylsilyl, diphenylisopropylsilyl, phenyldiisopropylsilyl and tert-butyldiphenylsilyl, and the "silyl group" is preferably trimethylsilyl, triethylsilyl, triisopropylsilyl, tert-butyldimethylsilyl or tert-butyldiphenylsilyl.

In the present specification, the "hydroxy-protecting group" and the protecting group of the "protected hydroxyl group" are not particularly limited as long as the hydroxyl group can be protected, and it is preferably a group capable of stably protecting a hydroxyl group upon synthesis of nucleic acid. To be specific, it is preferably a protecting group stable under an acidic or neutral condition and capable of cleaving due to chemical method such as hydrogenolysis, hydrolysis, electrolysis and photolysis.

Examples of such protecting group include
(a) an "acyl group";
(b) an "alkyl group";
(c) an "alkenyl group";
(d) a "tetrahydropyranyl group optionally substituted by 1 to 3 substituents selected from a halogen atom and alkoxy" and a "tetrahydrothiopyranyl group optionally substituted by 1 to 3 substituents selected from a halogen atom and alkoxy", such as tetrahydropyran-2-yl, 3-bromotetrahydropyran-2-yl, 4-methoxytetrahydropyran-4-yl, tetrahydrothiopyran-4-yl, 3-bromotetrahydrothiopyran-2-yl and 4-methoxytetrahydrothiopyran-4-yl;
(e) a "tetrahydrofuranyl group and tetrahydrothiofuranyl group" such as tetrahydrofuran-2-yl and tetrahydrothiofuran-2-yl;
(f) a "silyl group";
(g) an "alkoxy-alkyl group" such as methoxymethyl, 1-methoxy-1-methylethyl, ethoxymethyl, propoxymethyl, isopropoxymethyl, butoxymethyl, tert-butoxymethyl, 1-ethoxyethyl and 1-isopropoxyethyl;
(h) an "alkoxy-alkoxy-methyl group" such as 2-methoxyethoxymethyl;
(i) a "haloalkoxymethyl group" such as 2,2,2-trichloroethoxymethyl and bis(2-chloroethoxy)methyl;
(j) a "haloalkyl group" such as 2,2,2-trichloroethyl;
(k) a "methyl group substituted by 1 to 3 aryl groups" such as benzyl, α-naphthylmethyl, β-naphthylmethyl, diphenylmethyl, triphenylmethyl, α-naphthyldiphenylmethyl and 9-anthrylmethyl;
(l) a "methyl group substituted by 1 to 3 aryl groups optionally substituted by 1 to 3 substituents selected from alkyl, alkoxy, a halogen atom, cyano and nitro", such as 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 2-nitrobenzyl, 4-nitrobenzyl, 4-chlorobenzyl, 4-bromobenzyl and 4-cyanobenzyl;

(m) an "alkoxycarbonyl group" such as methoxycarbonyl, ethoxycarbonyl, tert-butoxycarbonyl and isobutoxycarbonyl;

(n) an "aryl group substituted by 1 to 3 substituents selected from a halogen atom, alkoxy and nitro" such as 4-chlorophenyl, 2-chlorophenyl, 4-methoxyphenyl, 4-nitrophenyl and 2,4-dinitrophenyl;

(o) an "alkoxycarbonyl group substituted by 1 to 3 substituents selected from a halogen atom and trialkylsilyl" such as 2,2,2-trichloroethoxycarbonyl and 2-trimethylsilylethoxycarbonyl;

(p) an "alkenyloxycarbonyl group" such as vinyloxycarbonyl and allyloxycarbonyl; and (q) an "aralkyloxycarbonyl group wherein the aryl ring is optionally substituted by 1 to 3 substituents selected from alkoxy and nitro" such as benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl.

The "hydroxy-protecting group" is preferably an "acyl group", a "methyl group substituted by 1 to 3 aryl groups", a "methyl group substituted by 1 to 3 aryl groups optionally substituted by 1 to 3 substituents selected from alkyl, alkoxy, a halogen atom, cyano and nitro" or a "silyl group", more preferably an acetyl group, a benzoyl group, a benzyl group, a p-methoxybenzoyl group, a 4,4'-dimethoxytriphenylmethyl group, a 4-methoxyphenyldiphenylmethyl group or a tert-butyldiphenylsilyl group. The protecting group of the "protected hydroxyl group" is preferably an "acyl group", a "methyl group substituted by 1 to 3 aryl groups", an "aryl group substituted by 1 to 3 substituents selected from a halogen atom, alkoxy and nitro", an "alkyl group" or an "alkenyl group", more preferably a benzoyl group, a benzyl group, a 2-chlorophenyl group, a 4-chlorophenyl group or a 2-propenyl group.

In the present specification, the "amino-protecting group" and the protecting group of the "protected amino group" are not particularly limited as long as the amino group can be protected, and it is preferably a group capable of stably protecting an amino group upon synthesis of nucleic acid. To be specific, it is preferably a protecting group stable under an acidic or neutral condition and capable of cleaving due to chemical method such as hydrogenolysis, hydrolysis, electrolysis and photolysis.

Examples of such protecting group include
(a) an "acyl group";
(b) an "alkoxycarbonyl group" such as methoxycarbonyl, ethoxycarbonyl, tert-butoxycarbonyl and isobutoxycarbonyl;
(c) an "alkoxycarbonyl group optionally substituted by 1 to 3 substituents selected from a halogen atom and trialkylsilyl" such as 2,2,2-trichloroethoxycarbonyl and 2-trimethylsilylethoxycarbonyl;
(d) an "alkenyloxycarbonyl group" such as vinyloxycarbonyl and allyloxycarbonyl;
(e) an "aralkyloxycarbonyl group wherein the aryl ring is optionally substituted by 1 to 3 substituents selected from alkoxy and nitro" such as benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl, and it is preferably an acyl group, more preferably a benzoyl group, an acetyl group or an isobutyryl group.

In the present specification, the "mercapto-protecting group" and the protecting group of the "protected mercapto group" are not particularly limited as long as the mercapto group can be protected, and it is preferably a group capable of stably protecting a mercapto group upon synthesis of nucleic acid. To be specific, it is preferably a protecting group stable under an acidic or neutral condition and capable of cleaving due to chemical method such as hydrogenolysis, hydrolysis, electrolysis and photolysis. Examples of such protecting group include those exemplified as the above-mentioned hydroxy-protecting group, and a "group capable of forming disulfide" such as an alkylthio group (e.g., methylthio, ethylthio, tert-butylthio), an arylthio group (e.g., benzylthio), and the like, and it is preferably an "acyl group" or a "methyl group substituted by 1 to 3 aryl groups", more preferably a benzoyl group or a benzyl group.

In the present specification, the "residue derived from a pyrimidine nucleobase" of the "residue derived from a pyrimidine nucleobase optionally having substituent(s)" means a group derived from a pyrimidine nucleobase (e.g., thymine, cytosine, uracil, 5-methylcytosine, 5-(hydroxymethyl)cytosine and the like) known as a constituent of nucleic acid, or a group derived from any chemical structure that can act or substitute as a pyrimidine nucleobase to be a constituent of a nucleic acid analogous thereto. These groups optionally have 1 to 5 substituents at substitutable position(s). Examples of such substituent include (a) a hydroxyl group,
(b) a protected hydroxyl group,
(c) an alkoxy group,
(d) a mercapto group,
(e) a protected mercapto group,
(f) an alkylthio group,
(g) an amino group,
(h) a protected amino group,
(i) an alkylamino group,
(j) an alkyl group,
(k) a halogen atom, and
(l) a triazolyl group. In addition, the above-mentioned "residue derived from a pyrimidine nucleobase" is optionally protected by a suitable "hydroxy-protecting group" or "amino-protecting group". The protecting group is preferably an acyl group, more preferably an acetyl group or a benzoyl group.

Moreover, the "residue derived from a pyrimidine nucleobase" is preferably a residue derived from a pyrimidine nucleobase, which is bonded, at the N1-position on the pyrimidine ring, to the carbon atom at 1-position on the adjacent sugar moiety. That is, in the reaction of the present invention, B is preferably a residue derived from a pyrimidine nucleobase optionally having substituent(s), and is bonded at the N1-position on the pyrimidine ring.

Preferable examples of the "residue derived from a pyrimidine nucleobase optionally having substituent(s)" include
a 2-oxo-4-amino-1,2-dihydropyrimidin-1-yl group (i.e., a cytosin-1-yl group),
a 2-oxo-4-amino-1,2-dihydropyrimidin-1-yl group protected by an amino-protecting group,
a 2-thio-4-amino-1,2-dihydropyrimidin-1-yl group,
a 2-thio-4-amino-1,2-dihydropyrimidin-1-yl group protected by an amino-protecting group,
a 2-oxo-4-amino-5-fluoro-1,2-dihydropyrimidin-1-yl group,
a 2-oxo-4-amino-5-fluoro-1,2-dihydropyrimidin-1-yl group protected by an amino-protecting group,
a 4-amino-2-oxo-5-chloro-1,2-dihydropyrimidin-1-yl group,
a 2-oxo-4-methoxy-1,2-dihydropyrimidin-1-yl group,
a 2-oxo-4-methoxy-1,2-dihydropyrimidin-1-yl group protected at the N3-position,
a 2-oxo-4-mercapto-1,2-dihydropyrimidin-1-yl group, a 2-oxo-4-mercapto-1,2-dihydropyrimidin-1-yl group protected at the N3-position or S4-position,
a 4-hydroxy-2-thio-1,2-dihydropyrimidin-1-yl group (i.e., a 2-thiouracil-1-yl group),
a 4-hydroxy-2-thio-1,2-dihydropyrimidin-1-yl group protected at the N3-position or O4-position,
a 2-oxo-4-hydroxy-1,2-dihydropyrimidin-1-yl group (i.e., an uracil-1-yl group),
a 2-oxo-4-hydroxy-1,2-dihydropyrimidin-1-yl group protected at the N3-position or O4-position,
a 2-oxo-4-hydroxy-5-methyl-1,2-dihydropyrimidin-1-yl group (i.e., a thymin-1-yl group),
a 2-oxo-4-hydroxy-5-methyl-1,2-dihydropyrimidin-1-yl group protected at the N3-position or O4-position,
a 4-hydroxy-2-thio-5-methyl-1,2-dihydropyrimidin-1-yl group,
a 4-hydroxy-2-thio-5-methyl-1,2-dihydropyrimidin-1-yl group protected at the N3-position or O4-position,
a 4-amino-5-methyl-2-oxo-1,2-dihydropyrimidin-1-yl group (i.e., 5-methylcytosin-1-yl group),
a 4-amino-5-methyl-2-oxo-1,2-dihydropyrimidin-1-yl group protected by an amino-protecting group,
a 4-amino-5-methyl-2-thio-1,2-dihydropyrimidin-1-yl group,
a 4-amino-5-methyl-2-thio-1,2-dihydropyrimidin-1-yl group protected by an amino-protecting group, and
a 2-oxo-5-methyl-1,2-dihydropyrimidin-1-yl group optionally having substituent(s).

More preferable examples of the "residue derived from a pyrimidine nucleobase optionally having substituent(s)" include
a 2-oxo-4-acetylamino-1,2-dihydropyrimidin-1-yl group,
a cytosin-1-yl group,
a thymin-1-yl group,
a 2-oxo-4-hydroxy-5-methyl-1,2-dihydropyrimidin-1-yl group protected at the N3-position or O4-position (preferably a 3-benzoyl-2-oxo-4-hydroxy-5-methyl-1,2-dihydropyrimidin-1-yl group (a 3-N-benzoylthymin-1-yl group)),
an uracil-1-yl group,
a 2-oxo-4-hydroxy-1,2-dihydropyrimidin-1-yl group protected at the N3-position or O4-position,
a 4-amino-5-methyl-2-oxo-1,2-dihydropyrimidin-1-yl group protected by an amino-protecting group (preferably a 2-oxo-4-acetylamino-5-methyl-1,2-dihydropyrimidin-1-yl group (a 4-N-acetyl-5-methylcytosin-1-yl group)),
a 5-methylcytosin-1-yl group, and
a 2-oxo-4-(triazol-1-yl)-5-methyl-1,2-dihydropyrimidin-1-yl group.

In another preferable embodiment, B is preferably a residue derived from a pyrimidine nucleobase protected by an amino-protecting group, and is bonded at the N1-position on the pyrimidine ring.

B is more preferably a 3-benzoyl-2-oxo-4-hydroxy-5-methyl-1,2-dihydropyrimidin-1-yl group (a 3-N-benzoylthymin-1-yl group) or a 2-oxo-4-acetylamino-5-methyl-1,2-dihydropyrimidin-1-yl group (a 4-N-acetyl-5-methylcytosin-1-yl group).

B is particularly preferably a residue derived from a thymine nucleobase wherein the nitrogen atom at the N3-position is protected by a benzoyl group, which is bonded at the N1-position on the pyrimidine ring, that is, a 3-benzoyl-2-oxo-4-hydroxy-5-methyl-1,2-dihydropyrimidin-1-yl group (a 3-N-benzoylthymin-1-yl group).

In the present specification, the "residue derived from a purine nucleobase" of the "residue derived from a purine nucleobase optionally having substituent(s)" means a group derived from a purine nucleobase (e.g., purine, adenine, guanine and the like) known as a constituent of a nucleic acid, a group derived from hypoxanthine, xanthine, theobromine, caffeine, uric acid, isoguanine and the like, or a group derived from any chemical structure that can act or substitute as a purine nucleobase to be a constituent of a nucleic acid analogous thereto. These groups optionally have 1 to 5 substituents at substitutable position(s). Examples of such substituent include
(a) a hydroxyl group,
(b) a protected hydroxyl group,
(c) an alkoxy group,
(d) a mercapto group,
(e) a protected mercapto group,
(f) an alkylthio group,
(g) an amino group,
(h) a protected amino group,
(i) an alkylamino group,
(j) an alkyl group, and
(k) a halogen atom. In addition, the above-mentioned "residue derived from a purine nucleobase" is optionally protected by a suitable "hydroxy-protecting group" or "amino-protecting group". The "residue derived from a purine nucleobase" is preferably a residue derived from a purine nucleobase wherein the nitrogen atom at the N9-position on the purine ring is bonded to the carbon atom at the 1-position on the adjacent sugar moiety. That is, in the reaction of the present invention, B' is preferably a residue derived from a purine nucleobase optionally having substituent(s), and is bonded at the N9-position on the purine ring.

The "residue derived from a purine nucleobase" is more preferably a residue derived from a purine nucleobase having a bulky substituent at the C6-position on the purine ring (when it is a residue derived from a purine nucleobase having a hydroxyl group or an amino group at the C6-position on the purine ring, the group is substituted by a bulky substituent).

The "bulky substituent" may be any substituent as long as the below-mentioned reaction (transglycosylation reaction) of the present invention can be controlled so that the transglycosylation reaction is performed at the nitrogen atom at the N9-position on the purine ring, not the nitrogen atom at the N7-position on the purine ring. Examples thereof include an acyl group or an amidine-type protecting group. The bulky substituent is preferably an acyl group, more preferably a phenoxyacetyl group, an acetyl group, a benzoyl group or a diphenylcarbamoyl group, particularly preferably a benzoyl group, an acetyl group or a diphenylcarbamoyl group.

That is, in the reaction of the present invention, B' is preferably a residue derived from a purine nucleobase having a bulky substituent at the C6-position on the purine ring and optionally having additional substituent(s), and is bonded at the N9-position on the purine ring.

Preferable examples of the "residue derived from a purine nucleobase" include
a 6-aminopurin-9-yl group (i.e., an adenin-9-yl group),
a 6-aminopurin-9-yl group protected by an amino-protecting group,
a 2,6-diaminopurin-9-yl group,
a 2-amino-6-chloropurin-9-yl group,
a 2-amino-6-chloropurin-9-yl group protected by an amino-protecting group,
a 2-amino-6-fluoropurin-9-yl group,
a 2-amino-6-fluoropurin-9-yl group protected by an amino-protecting group,
a 2-amino-6-bromopurin-9-yl group,
a 2-amino-6-bromopurin-9-yl group protected by an amino-protecting group, a 2-amino-6-hydroxypurin-9-yl group (i.e., a guanin-9-yl group),
a 2-amino-6-hydroxypurin-9-yl group protected by an amino-protecting group and a hydroxy-protecting group,
a 6-amino-2-methoxypurin-9-yl group,
a 6-amino-2-chloropurin-9-yl group,
a 6-amino-2-fluoropurin-9-yl group,
a 2,6-dimethoxypurin-9-yl group,
a 2,6-dichloropurin-2-yl group,
a 6-mercaptopurine-9-yl group,
a 6-chloropurine, and
a 2-amino-6-chloropurin-9-yl group.

More preferable examples of the "residue derived from a purine nucleobase" include
a 6-benzoylaminopurin-9-yl group (a 6-N-benzoyladenin-9-yl group),
a 6-acetylaminopurin-9-yl group (a 6-N-acetyladenin-9-yl group),
an adenin-9-yl group,
a 2-acetylamino-6-diphenylcarbamoyloxypurin-9-yl group (a 2-N-acetyl-6-O-diphenylcarbamoylguanin-9-yl group),
a 2-isobutyrylamino-6-hydroxypurin-9-yl group,
a guanin-9-yl group, and
a 2-amino-6-chloropurin-9-yl group.

In another preferable embodiment, B' is preferably a residue derived from a purine nucleobase having an amino group optionally protected by a benzoyl group at the C6-position, and is bonded at the N9-position on the purine ring, more preferably a 6-benzoylaminopurin-9-yl group (a 6-N-benzoyladenin-9-yl group).

In another preferable embodiment, B' is preferably a residue derived from a purine nucleobase having a hydroxyl group optionally protected by a diphenylcarbamoyl group at the C6-position, and optionally having an amino group protected by an amino-protecting group, and is bonded at the N9-position on the purine ring, more preferably a 2-acetylamino-6-diphenylcarbamoyloxypurin-9-yl group (a 2-N-acetyl-6-β-diphenylcarbamoylguanin-9-yl group).

In another preferable embodiment, B' is preferably a residue derived from a purine nucleobase having an oxo group at the C6-position, and optionally having an amino group protected by an amino-protecting group, and is bonded at the N9-position on the purine ring, more preferably a guanin-9-yl group.

In the present specification, examples of the "functional molecular unit substituent" include residues derived from labeling molecules (e.g., fluorescence·luminescence-labeling molecules, chemiluminescence-labeling molecules, molecular species containing radioactive isotope), residues derived from molecules with DNA- or RNA-cleavage activity, residues derived from intracellular signal peptides (e.g., residues derived from nuclear localization signal peptides), residues derived from membrane permeable peptides, and the like.

Compound (I) and compound (I') may be used in the form of a salt. Examples of the salt include metal salts such as alkali metal salts (e.g., sodium salt, potassium salt and lithium salt), alkaline earth metal salts (e.g., calcium salt and magnesium salt), aluminum salt, iron salt, zinc salt, copper salt, nickel salt, cobalt salt and the like; amine salts such as salts with inorganic base (e.g., ammonium salt), salts with organic base (e.g., tert-octylamine salt, dibenzylamine salt, morpholine salt, glucosamine salt, phenylglycine alkylester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzyl-phenethylamine salt, piperazine salt, tetramethylammonium salt and tris(hydroxymethyl)aminomethane salt) and the like; inorganic acid salts such as hydrohalides (e.g., hydrofluoride, hydrochloride, hydrobromide, hydroiodide), nitrate salt, perchlorate, sulfate, phosphate and the like; organic acid salts such as lower alkanesulfonates (e.g., methanesulfonate, trifluoromethanesulfonate, ethanesulfonate), arylsulfonates (e.g., benzenesulfonate, p-toluenesulfonate), acetate, maleate, fumarate, succinate, citrate, tartrate, oxalate, maleate and the like; and salts with amino acid such as glycinate, lysinate, argininate, ornithinate, glutamate and aspartate.

For practicing the present invention, compound (I) (pyrimidine nucleoside) and compound (I') (purine nucleoside) are each preferably the following compound:

(1) compound (I) and compound (I') wherein $R_1$ and $R_1'$ are each independently a hydrogen atom; an acyl group; an aliphatic or aromatic sulfonyl group; a methyl group substituted by 1 to 3 aryl groups; a methyl group substituted by 1 to 3 aryl groups optionally substituted by 1 to 3 substituents selected from the group consisting of alkyl, alkoxy, a halogen atom and cyano; or a silyl group;

(2) compound (I) and compound (I') wherein $R_1$ and $R_1'$ are each independently a hydrogen atom, an acetyl group, a benzoyl group, a methanesulfonyl group, a p-toluenesulfonyl group, a benzyl group, a p-methoxybenzyl group or a tert-butyldiphenylsilyl group (preferably compound (I) and compound (I') wherein $R_1$ and $R_1'$ are each a methanesulfonyl group);

(2') compound (I) and compound (I') wherein $R_1$ and $R_1'$ are each independently a hydrogen atom, an acetyl group, a benzoyl group, a methanesulfonyl group, a p-toluenesulfonyl group, a benzyl group or a tert-butyldiphenylsilyl group (preferably compound (I) and compound (I') wherein $R_1$ and $R_1'$ are each a methanesulfonyl group);

(3) compound (I) and compound (I') wherein $R_2$ and $R_2'$ are each independently a hydrogen atom; an acyl group; an aliphatic or aromatic sulfonyl group; a methyl group substituted by 1 to 3 aryl groups; a methyl group optionally substituted by 1 to 3 aryl group substituted by 1 to 3 substituents selected from the group consisting of alkyl, alkoxy, a halogen atom and cyano; or a silyl group;

(4) compound (I) and compound (I') wherein $R_2$ and $R_2'$ are each independently a hydrogen atom, an acetyl group, a benzoyl group, a methanesulfonyl group, a p-toluenesulfonyl group, a benzyl group, a p-methoxybenzyl group or a tert-butyldiphenylsilyl group (preferably compound (I) and compound (I') wherein $R_2$ and $R_2'$ are each a benzyl group);

(5) compound (I) and compound (I') wherein $R_1$ and $R_2$ in combination or $R_1'$ and $R_2'$ in combination form a group represented by the formula

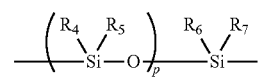

wherein $R_4$ in the number of p, $R_5$ in the number of p, $R_6$ and $R_7$ are each independently a $C_{1-6}$ alkyl group or an aryl group, and p is an integer of 1 to 3, (preferably compound (I) and compound (I') wherein $R_1$ and $R_2$ in combination or $R_1'$ and $R_2'$ in combination form a group represented by the formula

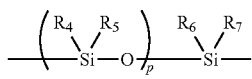

wherein
R$_4$ in the number of p, R$_5$ in the number of p, R$_6$ and R$_7$ are each independently a C$_{1-6}$ alkyl group, and
p is an integer of 1 to 3 (preferably 1));
(6) compound (I) and compound (I') wherein R$_3$ is a hydrogen atom, an alkyl group, an alkenyl group, an aryl group, a methyl group substituted by 1 to 3 aryl groups, an aliphatic or aromatic sulfonyl group, a phenoxyacetyl group or a functional molecular unit substituent wherein the functional molecular unit substituent is not particularly limited as long as it is a molecule capable of imparting a particular function to a pyrimidine nucleoside, purine nucleoside or a salt thereof of the present invention, preferably a residue derived from a fluorescence·luminescence-labeling molecule (e.g., a pyren-1-ylmethyl group) or a residue derived from a chemiluminescence-labeling molecule (e.g., an anthracen-2-ylmethyl group), a residue derived from a functional group with nucleic acid-cleavage activity (e.g., an imidazol-4-ylmethyl group), a residue derived from a membrane permeable peptide (e.g., octaarginine, TAT peptide) or a residue derived from a nuclear localization signal peptide (for example, -Pro-Pro-Lys-Lys-Lys-Arg-Lys-Val-)) (preferably compound (I) and compound (I') wherein R$_3$ is an alkyl group);
(7) compound (I) and compound (I') wherein m is 0 and n is 1;
(8) compound (I) and compound (I') wherein B is
a 2-oxo-4-acetylamino-1,2-dihydropyrimidin-1-yl group,
a cytosin-1-yl group,
a thymin-1-yl group,
a 2-oxo-4-hydroxy-5-methyl-1,2-dihydropyrimidin-1-yl group protected at the N3-position or O4-position (preferably a 3-benzoyl-2-oxo-4-hydroxy-5-methyl-1,2-dihydropyrimidin-1-yl group (a 3-N-benzoylthymin-1-yl group)),
an uracil-1-yl group,
a 2-oxo-4-hydroxy-1,2-dihydropyrimidin-1-yl group protected at the N3-position or O4-position,
a 4-amino-5-methyl-2-oxo-1,2-dihydropyrimidin-1-yl group protected by an amino-protecting group (preferably a 2-oxo-4-acetylamino-5-methyl-1,2-dihydropyrimidin-1-yl group (a 4-N-acetyl-5-methylcytosin-1-yl group)),
a 5-methylcytosin-1-yl group, or
a 2-oxo-4-(triazol-1-yl)-5-methyl-1,2-dihydropyrimidin-1-yl group;
(9) compound (I) and compound (I') wherein B' is
a 6-benzoylaminopurin-9-yl group (a 6-N-benzoyladenin-9-yl group),
a 6-acetylaminopurin-9-yl group (a 6-N-acetyladenin-9-yl group),
an adenin-9-yl group,
a 2-acetylamino-6-diphenylcarbamoyloxypurin-9-yl group (a 2-N-acetyl-6-O-diphenylcarbamoylguanin-9-yl group),
a 2-isobutyrylamino-6-hydroxypurin-9-yl group,
guanin-9-yl group, or
a 2-amino-6-chloropurin-9-yl group;
(10) compound (I) and compound (I') wherein R$_1$ and R$_1$' are each independently an aliphatic sulfonyl group (preferably methanesulfonyl),
R$_2$ and R$_2$' are each independently a methyl group substituted by 1 to 3 aryl groups (preferably benzyl), or R$_1$ and R$_2$ in combination or R$_1$' and R$_2$' in combination form a group represented by the formula

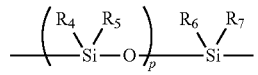

wherein
R$_4$ in the number of p, R$_5$ in the number of p$_5$, R$_6$ and R$_7$ are each independently a C$_{1-6}$ alkyl group (preferably isopropyl), and
p is an integer of 1 to 3 (preferably 1),
R$_3$ is an alkyl group (preferably a C$_{1-6}$ alkyl group, more preferably methyl),
B is
a thymin-1-yl group,
a 2-oxo-4-hydroxy-5-methyl-1,2-dihydropyrimidin-1-yl group protected at the N3-position (preferably a 3-benzoyl-2-oxo-4-hydroxy-5-methyl-1,2-dihydropyrimidin-1-yl group (a 3-N-benzoylthymin-1-yl group)),
a 4-amino-5-methyl-2-oxo-1,2-dihydropyrimidin-1-yl group protected by an amino-protecting group (preferably a 2-oxo-4-acetylamino-5-methyl-1,2-dihydropyrimidin-1-yl group (a 4-N-acetyl-5-methylcytosin-1-yl group)),
a 5-methylcytosin-1-yl group, or
a 2-oxo-4-(triazol-1-yl)-5-methyl-1,2-dihydropyrimidin-1-yl group,
B' is
a 6-benzoylaminopurin-9-yl group (a 6-N-benzoyladenin-9-yl group),
a 6-acetylaminopurin-9-yl group (a 6-N-acetyladenin-9-yl group),
an adenin-9-yl group,
a 2-acetylamino-6-diphenylcarbamoyloxypurin-9-yl group (a 2-N-acetyl-6-O-diphenylcarbamoylguanin-9-yl group),
a guanin-9-yl group, or
a 2-amino-6-chloropurin-9-yl group,
m is 0, and
n is 1.

The present invention is a transglycosylation from an NC type pyrimidine nucleoside to a purine nucleobase, and can be performed according to the following.

In the present invention, compound (I'), which is an NC type purine nucleoside, is synthesized from compound (I), which is an NC type pyrimidine nucleoside, as a starting material. The NC type pyrimidine nucleoside, which is a starting material, can be synthesized according to, for example, the method described in WO 2005/021570 or prior art of this field. The reaction conditions, protecting group introduction reagent, reaction reagent and the like are not limited to the method described in the above-mentioned document, and reaction conditions and reagents usable based on the technical common knowledge of the field can be appropriately employed.

The transglycosylation progresses by mixing compound (I) or a salt thereof with the purine nucleobase in the presence of a Lewis acid to produce compound (I') or a salt thereof.

Examples of the purine nucleobase include residues derived from purine nucleobases (e.g., purine, adenine, guanine and the like) known as a constituent of a nucleic acid, hypoxanthine, xanthine, theobromine, caffeine, uric acid, isoguanine and the like, and any chemical structure that can act or substitute as a purine nucleobase analogous thereto.

These groups optionally have 1 to 5 substituents at substitutable position(s). Examples of such substituent include
(a) a hydroxyl group,
(b) a protected hydroxyl group,
(c) an alkoxy group,
(d) a mercapto group,
(e) a protected mercapto group,
(f) an alkylthio group,
(g) an amino group,
(h) a protected amino group,
(i) an alkylamino group,
(j) an alkyl group, and
(k) a halogen atom. In addition, these "purine nucleobase" is optionally protected by a suitable "hydroxy-protecting group" or "amino-protecting group".

In the present invention, in order to achieve regioselectivity so that the obtained purine nucleoside is transglycosylated at the nitrogen atom at the N9-position on the purine ring (not transglycosylated at the nitrogen atom at the N7-position on the purine ring), the purine nucleobase desirably has a bulky substituent at the C6-position. The bulky substituent is as described above. The purine nucleobase having a bulky substituent can be obtained according to a method known per se. The amount of the purine nucleobase (including the purine nucleobase represented by the formula B'H) to be used is generally about 1 mol to about 20 mol, preferably about 3 mol to about 10 mol, per 1 mol of compound (I) or a salt thereof.

In the present invention, transglycosylation reaction is performed in the presence of a Lewis acid to promote the reaction at the N9-position on the purine ring. By performing the reaction in the presence of a Lewis acid, the transglycosylation reaction regioselectively progresses at the N9-position on the purine ring.

As a Lewis acid, a Lewis acid known per se can be applied. Preferable examples thereof include trimethylsilyl trifluoromethanesulfonate (TMSOTf). The amount of the Lewis acid to be used is generally about 0.5 mol to about 5 mol, preferably about 0.5 mol to about 2 mol, per 1 mol of compound (I) or a salt thereof.

In addition, the present invention is preferably performed in the presence of a silylating agent in addition to the Lewis acid. The silylating agent is not particularly limited as long as it is a silylating agent known per se and can silylate the above-mentioned purine nucleobase in this reaction. Examples thereof include N,O-bis-trimethylsilylacetamide (BSA), N,O-bis-silyltrifluoroacetamide (BSTFA), hexamethyldisilasane (HMDS), N,O-bis-tertiary butyldimethylsilylacetamide, N-(trimethylsilyl)diethylamine, N-(trimethylsilyl)dimethylamine, N-methoxy-N,O-bis(trimethylsilyl)carbamate, N-methyl-N-trimethylsilylacetamide, N-methyl-N-trimethylsilylheptafluorobutylamide, N-methyl-N-trimethylsilyltrifluoroacetamide and N-trimethylsilylacetamide. The silylating agent is preferably N,O-bis-trimethylsilylacetamide (BSA). The amount of the silylating agent to be used is generally about 1.5 mol to about 5 mol, preferably about 2 mol to about 3 mol, per 1 mol of the purine nucleobase (including the purine nucleobase represented by the formula B'H).

When the present invention is performed in the presence of a silylating agent, after the reaction, the resulting compound may be subjecting to the reaction for removal of the silyl group derived from the silylating agent. For example, when B' is a guanin-9-yl group or a 2-amino-6-chloropurin-9-yl group, the silyl group derived from the silylating agent is removed since the silyl group is introduced into the amino group at the 2-position on the purine ring. The reaction for removal of the silyl group is performed according to a method known per se using a mineral acid such as hydrochloric acid, sulfuric acid, nitric acid and the like.

The present invention is preferably performed in a solvent that does not adversely influence the reaction. Examples of the solvent include acetonitrile, toluene, dichloromethane, dichloroethane, THF and the aforementioned silylating agent. The solvent is more preferably acetonitrile or toluene, particularly preferably toluene. The amount of the solvent to be used is about 5- to about 100-fold weight relative to compound (I) or a salt thereof.

The reaction temperature in the present invention is generally about 20° C. to about 200° C., preferably about 60° C. to about 120° C., more preferably about 80° C. to about 120° C., from the aspects of N9-regioselective transglycosylation.

The reaction time is generally about 30 min to about 24 hr, preferably about 30 min to about 12 hr from the aspects of N9-regioselective transglycosylation.

In the above-mentioned method, The objective compound (I') can also be produced by using the purine nucleobase wherein the dissociative hydrogen atom is silylated, which is represented by the formula B'H wherein B' is a residue derived from a purine nucleobase optionally having substituent(s), instead of the silylating agent and the purine nucleobase represented by formula B'H wherein B' is a residue derived from a purine nucleobase optionally having substituent(s).

Examples of the purine nucleobase wherein the dissociative hydrogen atom is silylated, which is represented by the formula B'H, include, but are not limited to, a silylated N6-benzoyladenine represented by the formula

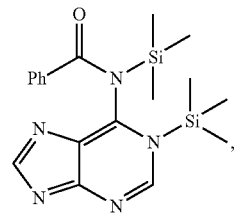 [SMILES: C[Si](C)(C)N(C(=O)c1ccccc1)c1c2ncnc-2ncn1[Si](C)(C)C]

a silylated N2-acetyl-O6-diphenylcarbamoylguanine represented by the formula

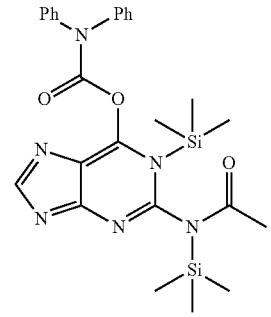 [SMILES: CC(=O)N(c1nc2ncnc-2c(OC(=O)N(c2ccccc2)c2ccccc2)n1[Si](C)(C)C)[Si](C)(C)C]

and the like.

The purine nucleobase wherein the dissociative hydrogen atom is silylated, which is represented by the formula B'H, may be produced using a commercially available product, or produced according to a method known per se (e.g., Synthesis 2005, No. 17, 2865-2870) or a method analogous thereto. The amount of the purine nucleobase wherein the dissociative hydrogen atom is silylated, which is represented by the formula B'H, to be used is generally about 1 mol to about 20 mol, preferably about 3 mol to about 10 mol, per 1 mol of compound (I) or a salt thereof.

Compound (I') or a salt thereof (hereinafter sometimes to be referred to as "the nucleoside of the present invention") can be converted into an oligonucleotide by applying the compound to a DNA synthesizer and the like together with compound (I) or other known nucleosides (natural nucleosides, artificial nucleosides and the like). The obtained oligonucleotide (hereinafter to be referred to as "the (oligo)nucleotide of the present invention") can be purified using a reverse-phase column. In addition, the production and purity of the purified oligonucleotide can be confirmed by analysis using a reverse-phase HPLC or MALDI-TOF-MS.

The oligonucleotide of the present invention can contain one or more nucleosides of the present invention. In addition, they may be present at one or more sites in the oligonucleotide of the present invention while being separated via one or more natural nucleotides. Moreover, an oligonucleotide containing a necessary number (length) of the nucleoside of the present invention at necessary position(s) introduced thereinto can be synthesized. The total length of the oligonucleotide of the present invention is 2 to 50, preferably 8 to 30, nucleotide units.

Since the oligonucleotide of the present invention contains the nucleoside of the present invention, it is not easily degraded by nuclease and can be present in the body for a long time after administration to the body. It can, for example, form a double strand with mRNA with high affinity to inhibit translation into a component (protein) to be the etiology, and can suppress gene expression due to degradation of the mRNA via endogenous RNase H. In addition, it is considered to inhibit an intracellular growth of an infected virus, or inhibit binding of a nucleotide-binding protein and a target cis-element sequence thereof.

From the above, the oligonucleotide of the present invention is expected to be useful as a "pharmaceutical product that treats a disease by inhibition of gene action" such as antitumor agents and antivirus agents. According to the present invention, therefore, an stable oligonucleotide analog having a superior antisense or antigene activity, or a superior activity as a superior detection drug for a particular gene or a primer for initiation of amplification, and a nucleoside analog, which is a production intermediate therefor, can be provided.

DNA and RNA oligonucleotide analogs (oligonucleotide analogs) obtained by modifying an NC type purine nucleoside, which is one of the nucleosides obtained by applying the present invention, are useful as various physiological or biological active substances, materials of pharmaceutical products, functional materials of double strand oligonucleotides for RNA interference method, decoy method and the like, functional materials of DNA chip, molecular beacon and the like targeting a single strand nucleic acid such as cDNA and the like, functional materials for use in various antisense methods (including ribozyme, DNAzyme), antigene method, and gene homologous recombinant method, materials for high sensitivity analysis of trace biological organic components by combination with fluorescence or luminescence substances, developmental materials of reagents for researches such as gene function analysis elucidation and the like.

The nucleosides of the present invention and the oligonucleotide of the present invention can be added with conventionally-used auxiliary, for example, a buffering agent and/or a stabilizer and the like to give a preparation for parenteral administration. In addition, as a topical preparation, ointment, cream, liquid, plaster and the like can be prepared by adding conventionally-used carriers for medicaments.

The present invention is explained more specifically in the following by referring to the following Examples and Reference Examples.

The abbreviations in the following Examples and Reference Examples mean the following.
Ms: methanesulfonyl group
Bn: benzyl group
DMTr: 4,4-dimethoxytrityl group

EXAMPLES

Example 1

Synthesis of BNA$^{NC}$-Adenosine Nucleoside

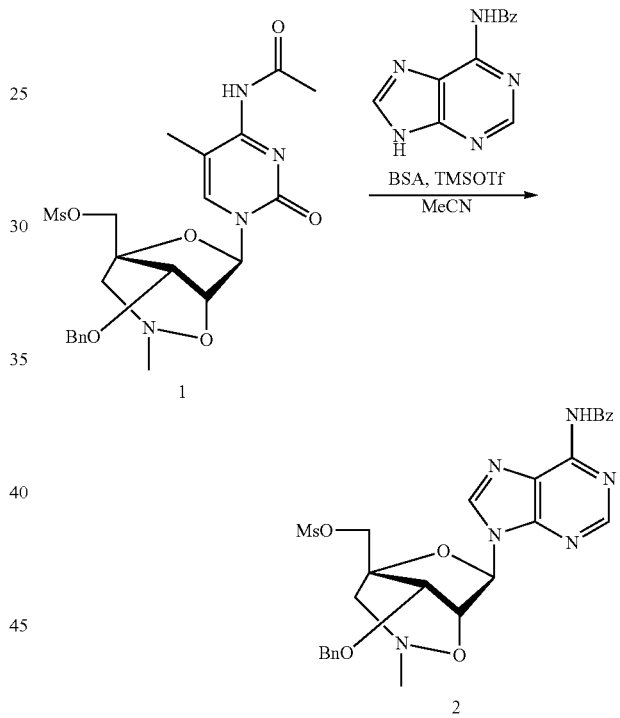

Compound 1 (50 mg, 0.1 mmol) and 6-N-benzoyladenine (119 mg, 0.5 mmol) were suspended in acetonitrile (1 ml). To the suspension was added N,O-bis-trimethylsilylacetamide (BSA), and the mixture was heated to 80° C., and then stirred for 10 min. To the reaction mixture was added trimethylsilyl trifluoromethanesulfonate (TMSOTf), and the mixture was stirred for additional 2 hr. The reaction mixture was cooled, diluted with ethyl acetate (50 ml), and washed with saturated aqueous sodium hydrogen carbonate solution, water and saturated brine (each 50 ml). The obtained organic layer was dried over sodium sulfate, and concentrated. The mixture was purified by reverse-phase HPLC (H$_2$O-MeCN, 0.05% TFA) to give compound 2 (2.8 mg, 5 μmol).

$^1$H NMR (600 MHz, CDCl$_3$) δ ppm 2.84 (s, 3H), 2.94 (d, J=11.00 Hz, 1H), 2.97 (s, 3H), 3.15 (d, J=11.00 Hz, 1H), 4.31-4.46 (m, 3H), 4.59 (d, J=11.74 Hz, 1H), 4.77 (d, J=11.74 Hz, 1H), 4.93 (d, J=2.20 Hz, 1H), 6.83 (s, 1H), 7.30-7.40 (m, 5H), 7.54 (t, J=7.70 Hz, 2H), 7.63 (t, J=7.34 Hz, 1H), 8.03 (d, J=7.70 Hz, 1H), 8.17 (s, 1H), 8.75 (s, 8.75 Hz, 1H), 9.06 (s, 1H).

Example 2

Synthesis of BNA$^{NC}$-Guanosine Nucleoside

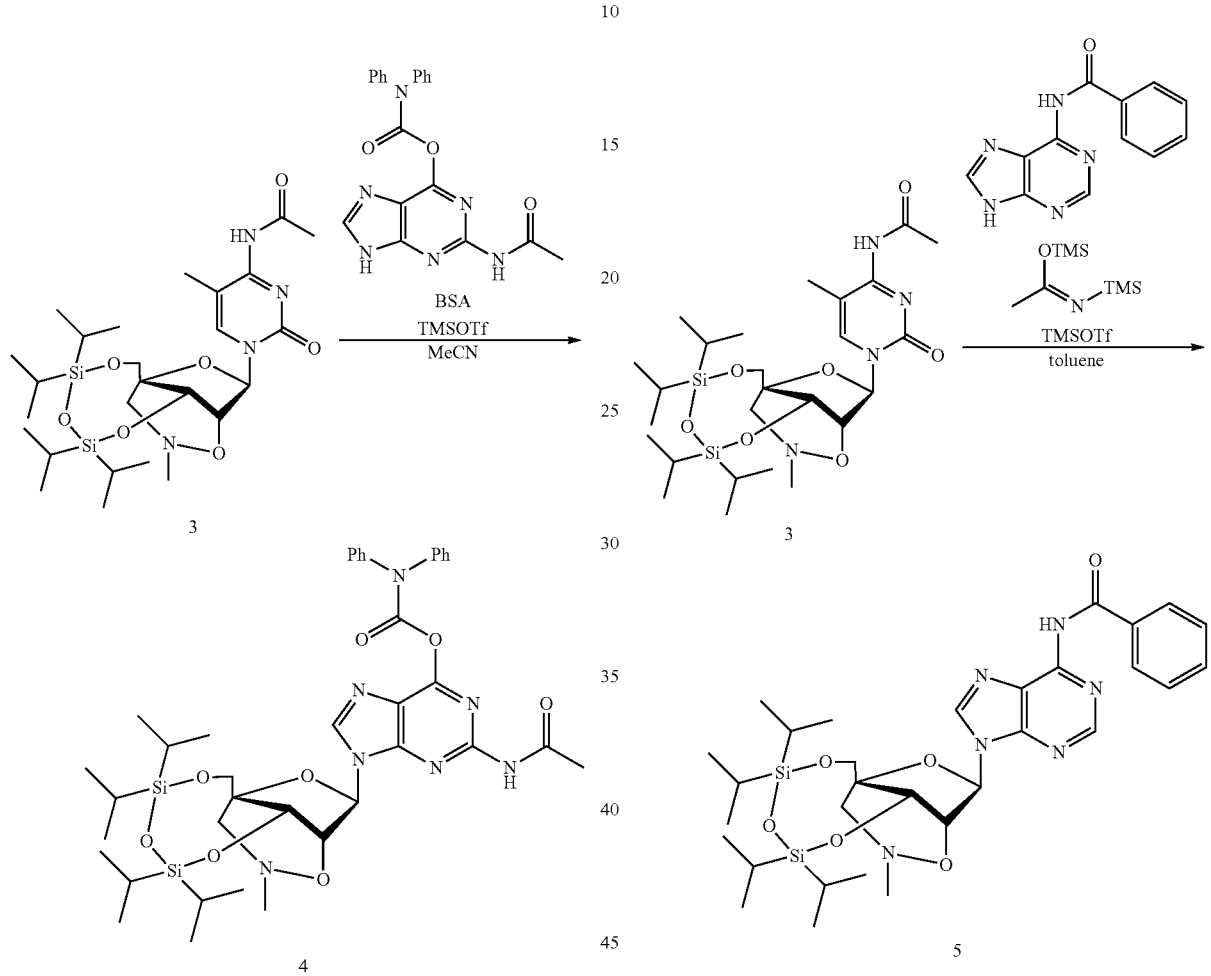

Compound 3 (58 mg, 0.1 mmol) and 2-N-acetyl-6-O-diphenylcarbamoylguanine (388 mg, 1 mmol) were suspended in acetonitrile (1 ml). To the suspension was added N,O-bis-trimethylsilylacetamide (BSA), and the mixture was stirred at room temperature for 30 min. The reaction mixture was warmed to 60° C., trimethylsilyl trifluoromethanesulfonate (TMSOTf) was added thereto, and the mixture was stirred for 5.5 hr. The reaction mixture was cooled, diluted with ethyl acetate (50 ml), and washed with saturated aqueous sodium hydrogen carbonate solution, water and saturated brine (each 50 ml). The obtained organic layer was dried over sodium sulfate. The insoluble material was removed by filtration, and the filtrate was concentrated. The mixture was purified by silica gel column chromatography (hexane-ethyl acetate) to give compound 4 (8.0 mg, 10 μmol).

$^1$H NMR (600 MHz, CDCl$_3$) δ ppm 0.77-1.19 (m, 28H), 2.60 (s, 3H), 2.67 (d, J=11.00 Hz, 1H), 2.79 (s, 3H), 2.98 (d, J=11.00 Hz, 1H), 3.72 (d, J=12.84 Hz, 1H), 4.06 (d, J=12.84 Hz, 1H), 4.22 (d, J=2.93 Hz, 1H), 4.53 (d, J=2.93 Hz, 1H), 6.63 (s, 1H), 7.12-7.56 (m, 10H), 8.02 (s, 1H), 8.29 (s, 1H).

Example 3

Synthesis of BNA$^{NC}$-Adenosine Nucleoside

Compound 3 (680 mg, 1.17 mmol) and 6-N-benzoyladenine (1.4 g, 5.9 mmol) were suspended in toluene (11 ml). To the suspension was added N,O-bis-trimethylsilylacetamide (BSA), and the mixture was heated to 100° C., and then stirred for 1 hr. To the reaction mixture was added trimethylsilyl trifluoromethanesulfonate (TMSOTf), and the mixture was stirred for additional 30 min. The reaction mixture was cooled, diluted with ethyl acetate (200 ml), and washed with saturated aqueous sodium hydrogen carbonate solution, water and saturated brine (each 100 ml). The obtained organic layer was dried over sodium sulfate, and concentrated. The mixture was purified by silica gel column chromatography (hexane-ethyl acetate) to give compound 5 (533 mg, 0.81 mmol).

$^1$H NMR (600 MHz, CDCl$_3$) δ 0.91-1.20 (m, 28H), 2.68 (d, J=11.00 Hz, 1H), 2.81 (s, 3H), 3.01 (d, J=11.00 Hz, 1H), 3.73 (d, J=12.84 Hz, 1H), 4.04 (d, J=12.84 Hz, 1H), 4.50 (d, J=2.93

Hz, 1H), 4.77 (d, J=2.57 Hz, 1H), 6.79 (s, 1H), 7.52 (t, J=7.70 Hz, 2H), 7.61 (t, J=7.30 Hz, 1H), 8.03 (d, J=7.70 Hz, 2H), 8.35 (s, 1H), 8.81 (s, 1H), 9.17 (s, 1H).

Example 4

Synthesis of BNA$^{NC}$-Guanosine Nucleoside

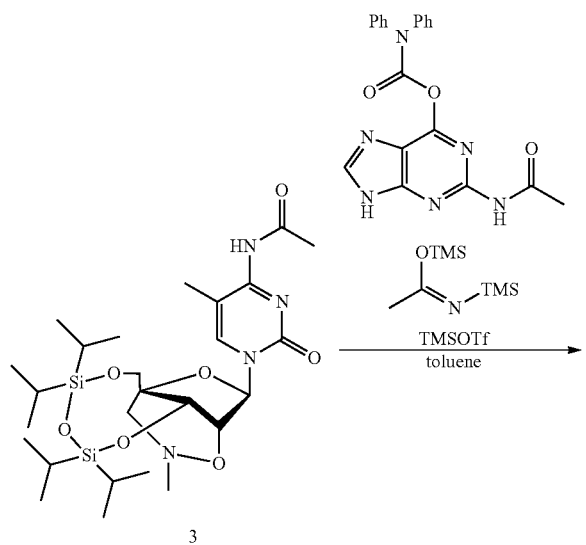

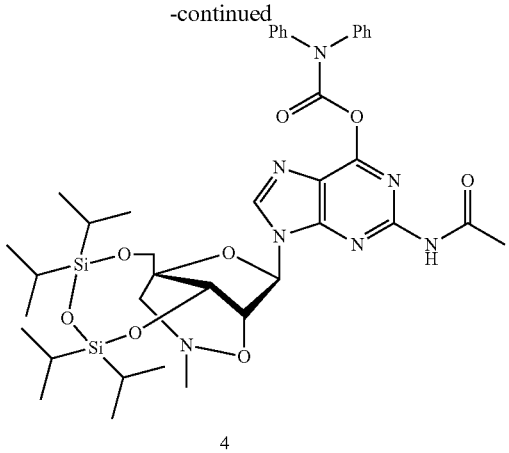

Compound 3 (1.0 g, 1.7 mmol) and 2-N-acetyl-6-β-diphenylcarbamoylguanine (3.6 g, 8.6 mmol) were suspended in toluene (10 ml). To the suspension was added N,O-bis-trimethylsilylacetamide (BSA), and the mixture was stirred at 100° C. for 30 min. To the reaction mixture was added trimethylsilyl trifluoromethanesulfonate (TMSOTf), and the mixture was stirred for additional 30 min. The reaction mixture was cooled, diluted with ethyl acetate (50 ml), and washed with saturated aqueous sodium hydrogen carbonate solution, water and saturated brine (each 50 ml). The obtained organic layer was dried over sodium sulfate. The insoluble material was removed by filtration, and the filtration was concentrated. The mixture was purified by silica gel column chromatography (hexane-ethyl acetate) to give compound 4 (325 mg, 0.4 mmol). The property values are the same as those in Example 2.

Example 5

Synthesis of BNA$^{NC}$-Adenosine Nucleoside

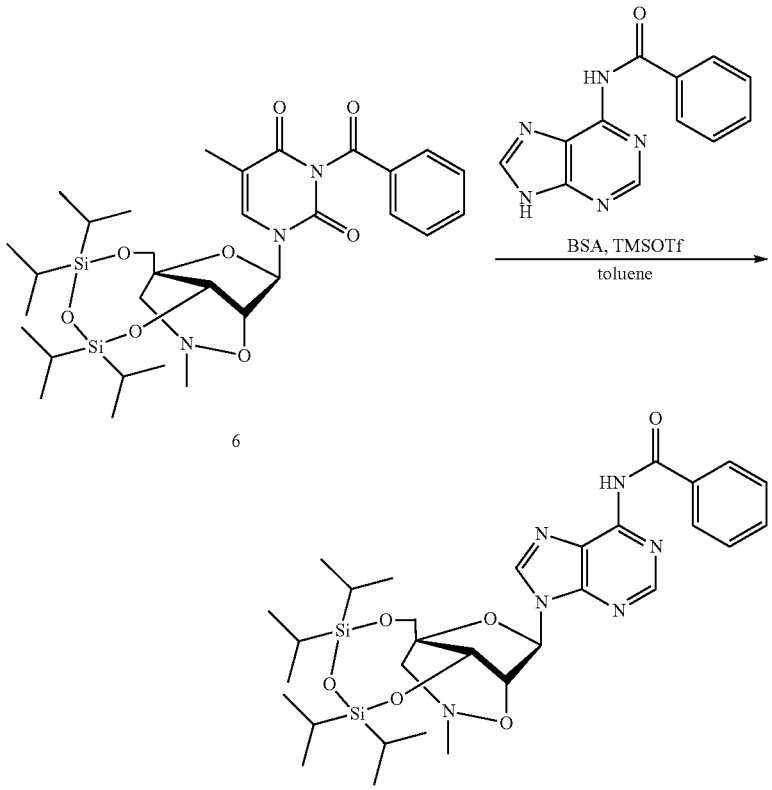

Compound 6 (300 mg, 0.46 mmol) and 6-N-benzoyladenine (300 mg, 0.46 mmol) were suspended in toluene (4.0 ml). To the obtained suspension was added BSA (1.15 ml, 4.6 mmol), and the mixture was refluxed for 1 hr. After cooling the refluxed solution until refluxing ceased, to the obtained solution was added TMSOTf (0.25 ml, 1.39 mmol), and the mixture was refluxed for 4.5 hr. After cooling the refluxed solution to room temperature, to the solution was added saturated aqueous sodium hydrogen carbonate solution (5.0 ml), and the reaction mixture was filtered through celite (washed with pyridine (30 ml)), and the filtrate was recovered. To the recovered filtrate was added ethyl acetate (30 ml), and the ethyl acetate layer was separated. To the obtained ethyl acetate layer was added saturated aqueous sodium hydrogen carbonate solution (containing NaCl), and the organic layer and the saturated aqueous sodium hydrogen carbonate solution layer were separated. The recovered saturated aqueous sodium hydrogen carbonate solution layer was reverse-extracted with ethyl acetate-tetrahydrofuran (1:1, v/v, 20 ml). The above-mentioned organic layer and the ethyl acetate-tetrahydrofuran solution used in the reverse-extraction were mixed. To the mixed organic layer was added magnesium sulfate, and then silica gel (3.0 g). The solvent of the organic layer was evaporated under reduced pressure to give a residue. The residue was purified by silica gel column chromatography (hexane:ethyl acetate=4:6-6:4, v/v) to give compound 5 (220% mg, 72%) as a white foamy solid.

Example 6

Synthesis of BNA$^{NC}$-Guanosine Nucleoside

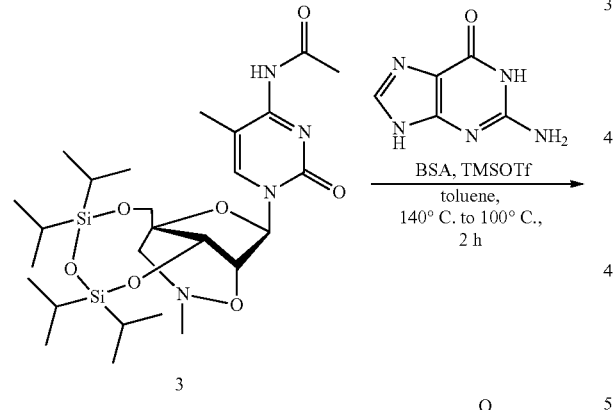

3

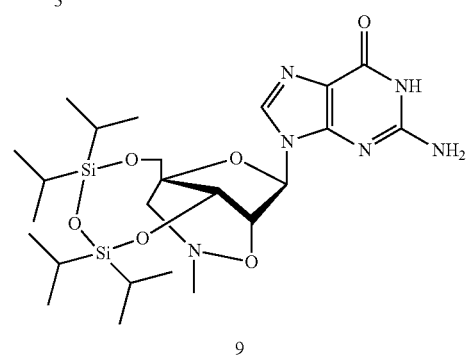

9

Guanine (775 mg, 5.13 mmol) was suspended in BSA (10 ml, 40.9 mmol) and toluene (10 ml), and the obtained suspension was refluxed for 1 hr. To the solution after refluxing was added TMSOTf (60 μl, 0.33 mmol), and the obtained suspension was refluxed until it became transparent. The solution after refluxing was cooled to 100° C., and to the solution were added compound 3 (1.0 g, 1.71 mmol) and TMSOTf (300 μl, 1.65 mmol). The obtained solution was added to a mixed solution (130 ml) of pyridine-methanol-water-triethylamine (100:10:20:1, v/v/v/v). The obtained solution was concentrated, and filtrated through celite, and the filtrate was recovered. The recovered filtrate was concentrated to give compound 9 (484 mg, 50%) as a pale-yellow solid.

$^{1}$H NMR (300 MHz, DMSO-d$_{6}$) δ 0.89-1.12 (28H, m), 2.66 (3H, s), 2.78 (2H, s), 3.67 (1H, d, J=13.2 Hz), 3.97-4.05 (1H, m), 4.20 (1H, d, J=3.2 Hz), 4.49 (1H, d, J=3.0 Hz), 6.35 (1H, s), 6.61 (2H, brs), 7.63 (1H, s), 10.64 (1H, s).

Example 7

Synthesis of BNA$^{NC}$-Guanosine Nucleoside

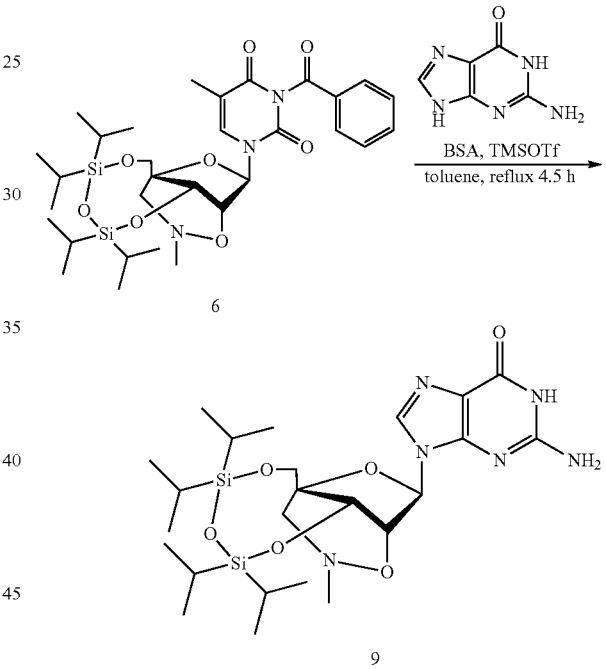

Guanine (351 mg, 2.32 mmol) was suspended in toluene (8.0 ml), and the obtained suspension was heated to refluxing temperature. To the solution after heating was added BSA (3.83 ml, 15.5 mmol, 20 equivalents), and the obtained solution was refluxed for 15 min. To the solution after refluxing was added TMSOTf (0.028 ml, 0.16 mmol), and the solution was refluxed until it became transparent. The solution after refluxing was cooled until refluxing ceased. To the solution after cooling were added compound 6 (500 mg, 0.77 mmol) and TMSOTf (0.14 ml, 0.77 mmol), and the obtained solution was refluxed for 4 hr. The solution after refluxing was cooled to room temperature. To the solution after cooling was added pyridine-triethylamine-distillation water (3:1:1, v/v/v, 3.0 ml), and the obtained solution was filtered through celite (washed with pyridine (30 ml)), and the filtrate was recovered. To the recovered filtrate was added ethyl acetate (30 ml), and the ethyl acetate layer was separated. The separated ethyl acetate layer was washed with distillation water (40 ml) and saturated aqueous sodium hydrogen carbonate solution (containing NaCl). The distilled water and saturated aqueous sodium hydrogen carbonate solution used in the washing were reverse-extracted with ethyl acetate-tetrahydrofuran (1:1, v/v, 20 ml). The ethyl acetate layer after washing and the ethyl acetate-tetrahydrofuran used in the reverse-extraction were mixed. To the mixed organic layer was added magnesium sulfate, and then silica gel (5.0 g). The solvent of the obtained solution was evaporated under reduced pressure to give a residue. The residue was purified by silica gel column chromatography (ethyl acetate:methanol=10:0-7:3, v/v). The objective fraction was concentrated under reduced pressure, and hexane-ethyl acetate (1:1, v/v) solution was added thereto. The precipitate formed in the solution was collected by filtration to give compound 9 (220 mg, 50%) as a white solid.

Example 8

Synthesis of BNA$^{NC}$-Adenosine Nucleoside reaction mixture were added saturated sodium hydrogen carbonate (568 ml) and ethyl acetate (568 ml), and the mixture was stirred at 0° C. for 15 min. The insoluble material formed in the solution after stirring was high-flow-precoat-filtrated, and the filtrate was recovered. To the recovered filtrate were added ethyl acetate (568 ml) and saturated brine (100 ml), and the ethyl acetate layer was separated. To the obtained ethyl acetate layer were added saturated brine (568 ml) and magnesium sulfate. The obtained solution was concentrated under reduced pressure to give a residue (41.5 g). The residue was purified by silica gel (420 g) chromatography (hexane:ethyl acetate=1:1, v/v). The effective fraction was collected and concentrated to give compound 5 as a pale-yellow foamy substance. yield 28.9 g (yield 79.4%).

Example 9

Synthesis of BNA$^{NC}$-Adenosine Nucleoside

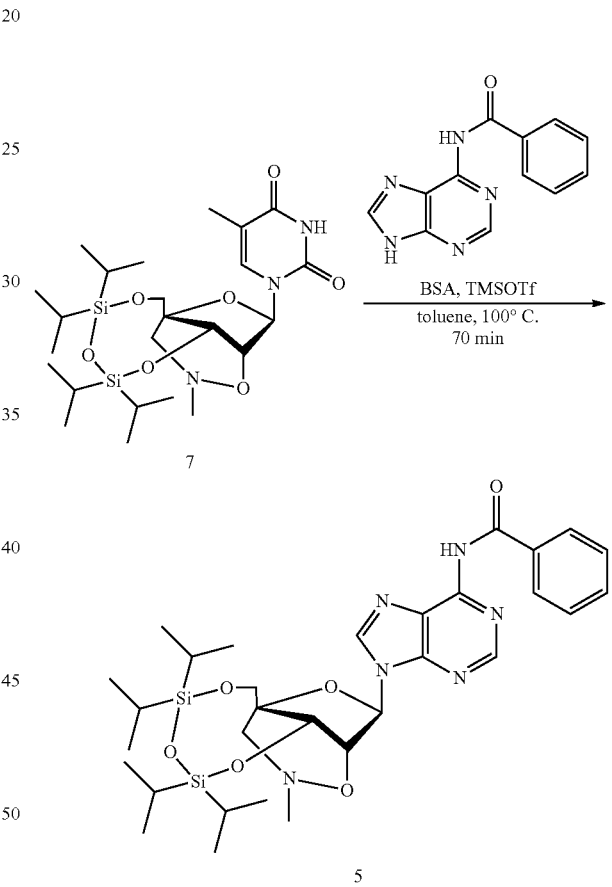

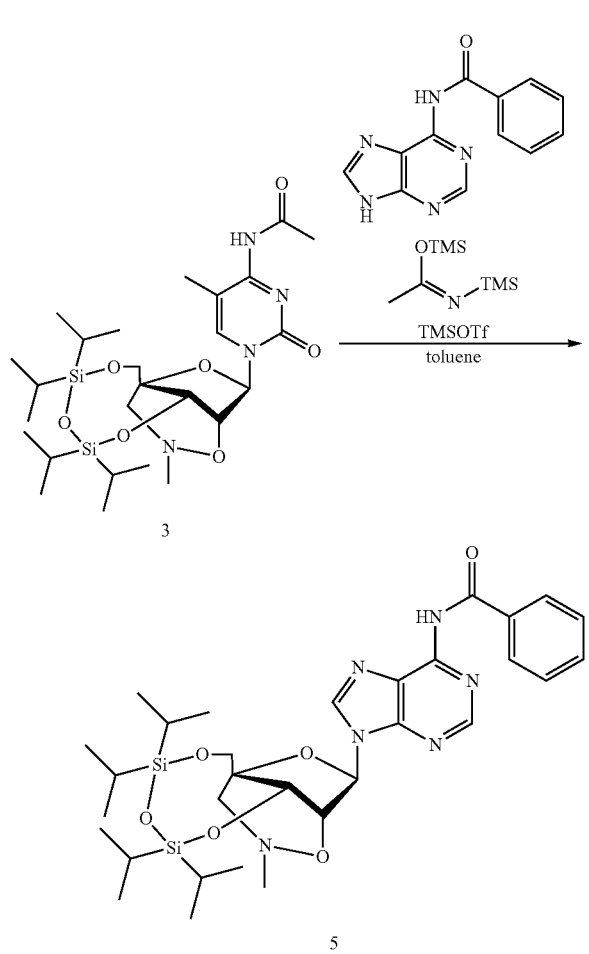

Compound 3 (32.4 g, 55.6 mmol) and 6-N-benzoyladenine (39.9 g, 166.8 mmol) were suspended in toluene (454 ml). To the obtained suspension was added BSA (67.8 g, 335.5 mmol), and the obtained suspension was stirred at 80-85° C. for 40 min. To the solution after stirring was added TMSOTf (37.1 g, 166.8 mmol), and the obtained solution was stirred for 30 min. The solution after stirring was cooled, and to the Compound 7 (270 mg, 0.5 mmol) and 6-N-benzoyladenine (359 mg, 1.5 mmol) were suspended in toluene (5 ml), and to obtained suspension was added BSA (1.1 ml, 4.5 mmol). The obtained suspension was heated at 100° C. until it became transparent, and to the obtained solution was added TMSOTf (118 μL, 0.65 mmol), and the mixture was stirred at 100° C. for 40 min. The solution after stirring was poured into saturated aqueous sodium hydrogen carbonate solution (40 ml), and to the obtained solution was added ethyl acetate (30 ml). The obtained solution was filtrated, the filtrate was recovered, and the ethyl acetate layer was separated from the recovered filtrate. To the obtained ethyl acetate layer was added saturated aqueous sodium hydrogen carbonate solution. The organic layer was separated from the obtained solution, and to the obtained organic layer was added anhydrous sodium sulfate. The solvent of the obtained solution was evaporated under reduced pressure to give a residue. The residue was purified by silica gel column chromatography (hexane:ethyl acetate=1:1, v/v) to give compound 5 (95 mg, 29%) as a white foamy solid.

Example 10

Synthesis of BNA$^{NC}$-Adenosine Nucleoside $^1$H NMR (300 MHz, DMSO-d$_6$) δ 0.89-1.13 (28H, m), 2.69 (3H, s), 2.73-2.87 (2H, m), 3.66 (1H, d, J=13.0 Hz), 3.97 (1H, d, J=13.2 Hz), 4.59 (1H, d, J=3.2 Hz), 4.79 (1H, d, J=3.0 Hz), 6.57 (1H, s), 7.35 (2H, brs), 8.08 (1H, s), 8.13 (1H, s).

Example 11

Synthesis of BNA$^{NC}$-Guanosine Nucleoside

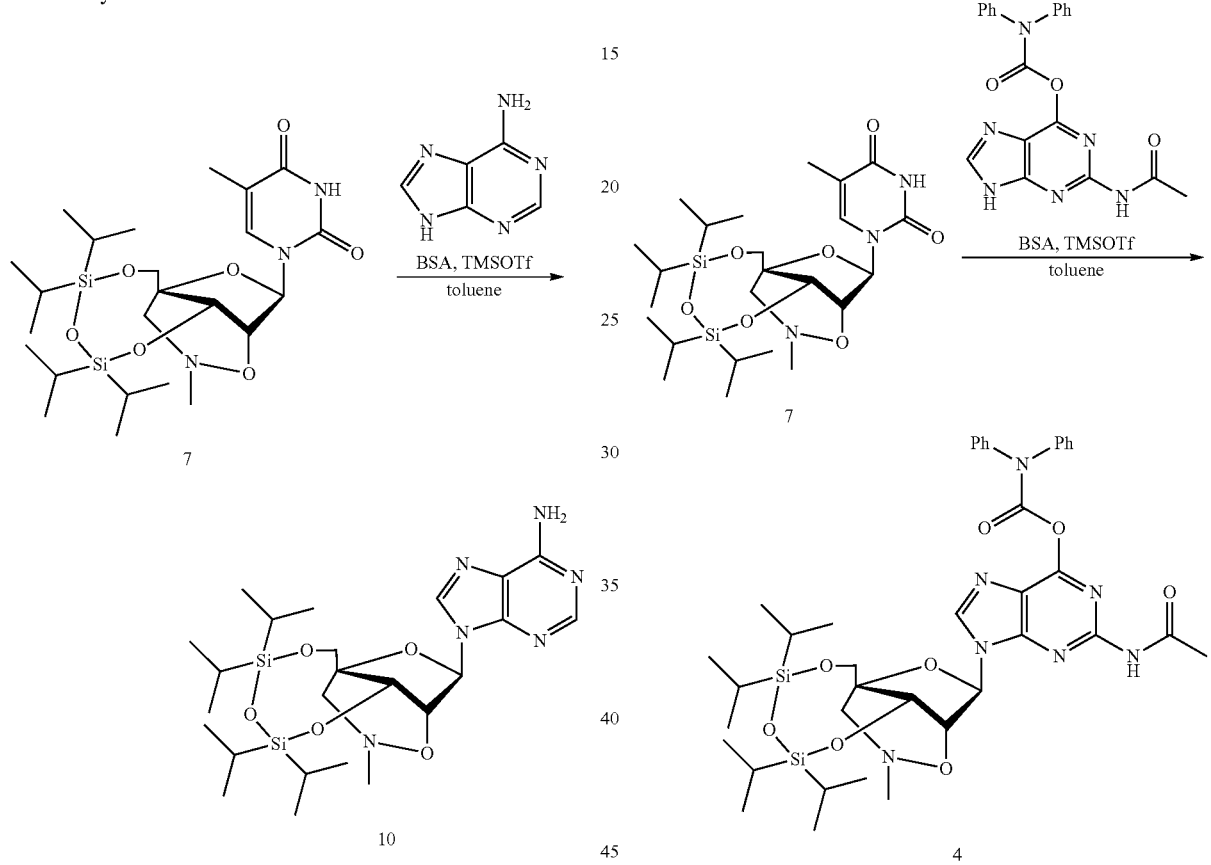

Adenine (135 mg, 1.5 mmol) was suspended in toluene (5.0 ml), and to the obtained suspension were added BSA (1.1 ml, 4.5 mmol) and TMSOTf (26 μL, 0.15 mmol). The obtained suspension was stirred at 100° C. until it became transparent. To the solution after stirring were added compound 7 (270 mg, 0.5 mmol) and TMSOTf (90 μL, 0.5 mmol), and the obtained solution was stirred at 100° C. for 30 min. The solution after stirring was cooled to room temperature, and to the solution was added ethyl acetate (30 ml). The obtained solution was separated to give an ethyl acetate layer. The obtained ethyl acetate layer was washed twice with saturated aqueous sodium hydrogen carbonate solution (40 ml). To the obtained ethyl acetate layer after washing was added anhydrous sodium sulfate. The solvent of the obtained solution was evaporated to give a residue. The residue was purified by silica gel column chromatography (hexane:ethyl acetate=4:6, v/v) to give compound 10 as a white solid. (110 mg, 40%)

2-N-Acetyl-6-O-diphenylcarbamoylguanine (624 mg, 1.5 mmol) was suspended in toluene (5 ml), and to the obtained suspension was added BSA (732 μL, 3 mmol). The obtained suspension was stirred at 100° C. until it became transparent. To the solution after stirring were added compound 7 and TMSOTf (118 μL, 0.65 mmol), and the obtained solution was stirred at 100° C. for additional 1 hr. To the solution after stirring were added saturated aqueous sodium hydrogen carbonate solution and ethyl acetate (40 ml), and the solution was separated, and the filtrate was recovered. To the recovered filtrate was added ethyl acetate, and the obtained solution was washed with saturated aqueous sodium hydrogen carbonate solution. The solution after washing was separated to give an organic layer. To the obtained organic layer was added anhydrous sodium sulfate. The solvent of the obtained solution was evaporated under reduced pressure to give a residue. The residue was purified by silica gel column chromatography (hexane:ethyl acetate=1:1, v/v) to give compound 4 (187 mg, 47%) as a pale-yellow foamy solid.

Example 12

Synthesis of BNA^NC-Guanosine Nucleoside

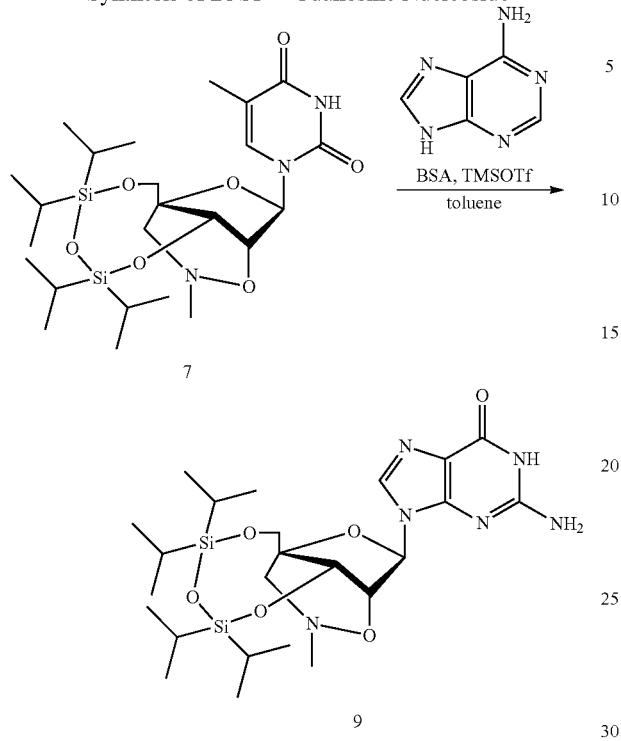

Guanine (227 mg, 1.5 mmol) was suspended in toluene (5 ml), and to the obtained suspension were added BSA (1.1 ml, 4.5 mmol) and TMSOTf (0.26 µL, 0.15 mmol). The obtained suspension was stirred at 100° C. until it became transparent. To the solution after stirring were added compound 7 (270 mg, 0.5 mmol) and TMSOTf (90.4 µL, 0.5 mmol), and the reaction mixture was stirred at 100° C. for 1 hr. The solution after stirring was cooled to room temperature, and the solution was poured into saturated aqueous sodium hydrogen carbonate solution. To the obtained solution was added ethyl acetate (30 ml). The obtained solution was filtered through celite, and the filtrate was recovered. The recovered filtrate was washed twice with saturated aqueous sodium hydrogen carbonate solution, and the organic layer was separated from the solution after washing. To the obtained organic layer was added sodium sulfate, and the solvent of the obtained solution was evaporated under reduced pressure to give a residue. The residue was purified by silica gel column chromatography (ethyl acetate:methanol=10:0-7:3, v/v). The objective fraction was concentrated to dryness under reduced pressure to give compound 9 (90 mg, 32%) as a white solid.

Example 13

Synthesis of BNA^NC-Adenosine Nucleoside

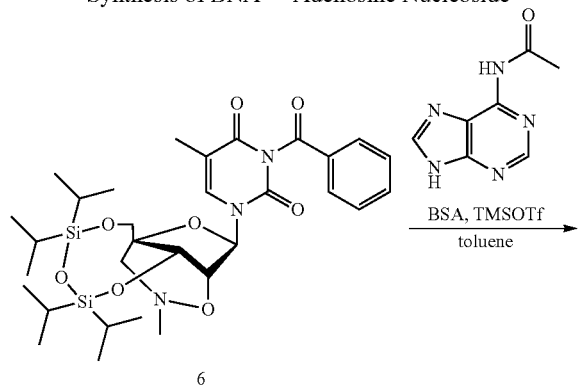

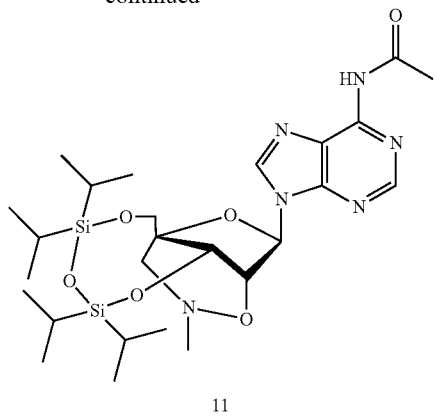

Compound 6 (500 mg, 0.77 mmol) and 6-N-acetyladenine (411 mg, 2.32 mmol) were suspended in toluene (8.0 ml), and to the obtained suspension was added BSA (1.15 ml, 4.6 mmol). The obtained suspension was refluxed for 1 hr. The solution after refluxing was cooled until refluxing ceased, and to the solution was added TMSOTf (0.17 ml, 0.93 mmol), and the obtained solution was refluxed for 4 hr. The solution after refluxing was cooled to room temperature, and to the solution was added pyridine-triethylamine-distillation water (3:1:1, v/v/v, 5.0 ml). The obtained solution was filtered through celite (washed with pyridine (30 ml)), and the filtrate was recovered. To the recovered filtrate was added ethyl acetate (30 ml), and the obtained solution was separated to give an organic layer. The obtained organic layer was washed twice with saturated aqueous sodium hydrogen carbonate solution (containing NaCl), and the saturated aqueous sodium hydrogen carbonate solution used in the washing was reverse-extracted with ethyl acetate-tetrahydrofuran (1:1, v/v, 20 ml). The organic layer after washing and the ethyl acetate-tetrahydrofuran used in the reverse-extraction were mixed. To the mixed organic layer was added magnesium sulfate and silica gel (5.0 g). The solvent of the obtained solution was evaporated under reduced pressure to give a residue. The residue was purified by silica gel column chromatography (hexane:ethyl acetate=6:4-2:8, v/v). The objective fraction was concentrated under reduced pressure, and to the residue was added hexane-ethyl acetate (1:1, v/v), and the precipitate was collected by filtration to give compound 11 (150 mg, 33%) as a white solid.

$^1$H NMR (300 MHz, CDCl$_3$) δ 0.90-1.17 (28H, m), 2.58-2.71 (4H, m), 2.81 (3H, s), 3.00 (1H, d, J=11.1 Hz), 3.73 (1H, d, J=12.8 Hz), 4.04 (1H, d, J=12.8 Hz), 4.46 (1H, d, J=3.2 Hz), 4.72 (1H, d, J=3.0 Hz), 6.75 (1H, s), 8.32 (1H, s), 8.53 (1H, s), 8.68 (1H, s).

Example 14

Synthesis of BNA$^{NC}$-Adenosine Nucleoside

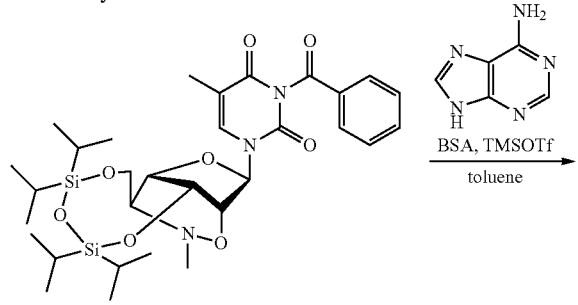

Adenine (314 mg, 2.32 mmol) was suspended in toluene (5.0 ml), and the obtained suspension was heated to refluxing temperature. To the obtained suspension were added BSA (3.84 ml, 15.5 mmol) and TMSOTf (0.028 ml, 0.16 mmol), and the obtained suspension was refluxed until it became transparent. The solution after refluxing was cooled until refluxing ceased, and compound 6 (500 mg, 0.77 mmol, toluene solution, 3 ml) and TMSOTf (0.14 ml, 0.77 mmol) were added thereto. The obtained solution was refluxed for 1.5 hr. The solution after refluxing was cooled to room temperature, and to the obtained solution was added pyridine-triethylamine-distillation water (3:1:1, v/v/v, 5.0 ml). The obtained solution was filtered through celite (washed with pyridine (30 ml)), and the filtrate was recovered. To the recovered filtrate was added ethyl acetate (30 ml), and the obtained solution was separated to give an organic layer. The obtained organic layer was washed twice with saturated aqueous sodium hydrogen carbonate solution (containing NaCl), the saturated aqueous sodium hydrogen carbonate solution used in the washing was reverse-extracted with ethyl acetate-tetrahydrofuran (1:1, v/v, 20 ml). The organic layer after washing and the ethyl acetate-tetrahydrofuran used in the reverse-extraction were mixed. To the organic layer were added magnesium sulfate and silica gel (5.0 g). The solvent of the obtained organic layer was evaporated under reduced pressure to give a residue. The residue was purified by silica gel column chromatography (hexane:ethyl acetate=50:50-0:100, v/v). The objective fraction was concentrated under reduced pressure, and to the residue was added hexane-ethyl acetate (1:1, v/v). The precipitate in the obtained solution was collected by filtration to give compound 10 (95 mg, 22%) as a white solid.

Example 15

Synthesis of BNA$^{NC}$-Guanosine Nucleoside

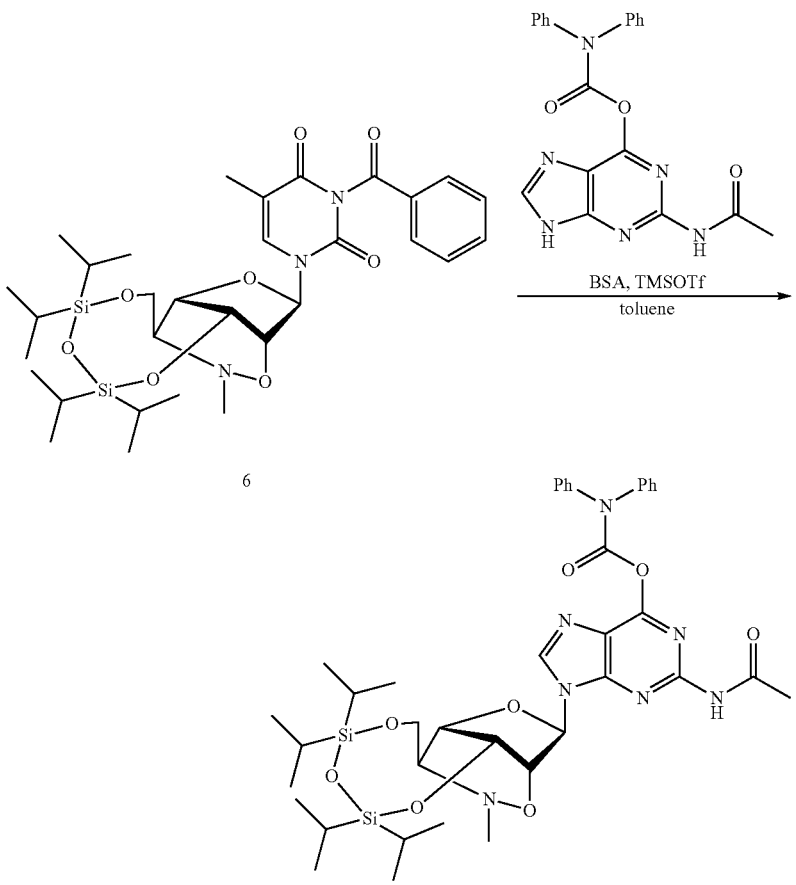

2-N-Acetyl-6-O-diphenylcarbamoylguanine (902 g, 2.32 mmol) was suspended in toluene (5.0 ml), and the obtained suspension was heated to refluxing temperature. To the heated suspension were added BSA (1.92 ml, 7.74 mmol) and TMSOTf (0.028 ml, 0.16 mmol), and the obtained suspension was refluxed for 30 min. After refluxing, the solution was cooled until refluxing ceased, and to the solution were added compound 6 (500 mg, 0.77 mmol, toluene solution, 3 ml) and TMSOTf (0.14 ml, 0.77 mmol, 1.0 eq). The obtained solution was refluxed for 4 hr. After refluxing, the solution was cooled to room temperature, and to the solution was added pyridine-triethylamine-distillation water (3:1:1, v/v/v, 5.0 ml). To the obtained solution was added ethyl acetate (30 ml). The obtained solution was separated to give an organic layer. The obtained organic layer was washed with distillation water (40 ml) and saturated aqueous sodium hydrogen carbonate solution (containing NaCl). The saturated aqueous sodium hydrogen carbonate solution used in the washing was reverse-extracted with ethyl acetate-tetrahydrofuran (1:1, v/v, 20 ml). The organic layer after washing and the ethyl acetate-tetrahydrofuran used in the reverse-extraction were mixed. To the mixed organic layer were added magnesium sulfate and silica gel (5.0 g). The solvent of the obtained solution was evaporated under reduced pressure to give a residue. The residue was purified by silica gel column chromatography (hexane: ethyl acetate=65:35-0:100, v/v) to give compound 4 (72 mg, 12%) as a white foamy solid.

Example 16

Synthesis of BNA$^{NC}$-Adenosine Nucleoside

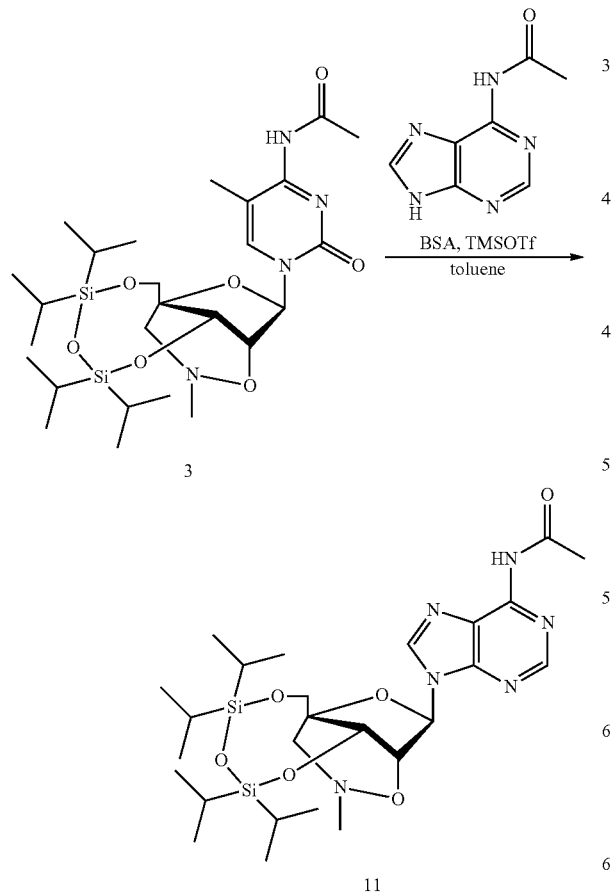

6-N-Acetyladenine (290 mg, 0.5 mmol) was suspended in toluene (5 ml), and to the obtained suspension were added BSA (732 μL, 3 mmol) and TMSOTf (30 μL, 0.17 mmol). The obtained suspension was heated at 100° C., and then stirred for 30 min. To the solution after stirring were added compound 3 (290 mg, 0.5 mmol) and TMSOTf (88 μL, 0.48 mmol), and the mixture was stirred for additional 30 min. The obtained solution was poured into saturated aqueous sodium hydrogen carbonate solution (30 ml), and the mixture was stirred for 10 min. To the solution after stirring was added ethyl acetate (40 ml). The obtained solution was filtrated, and the filtrate was recovered. The recovered filtrate was separated to give an organic layer. The obtained organic layer was washed with saturated aqueous sodium hydrogen carbonate solution. The organic layer obtained after washing was added aqueous anhydrous sodium sulfate solution, and the obtained solution was concentrated under reduced pressure to give a residue. The obtained residue was purified by silica gel column chromatography (hexane:ethyl acetate=2:8-0:10, v/v) to give compound 11 (235 mg, 79%) as white crystals.

Example 17

Synthesis of BNA$^{NC}$-Adenosine Nucleoside

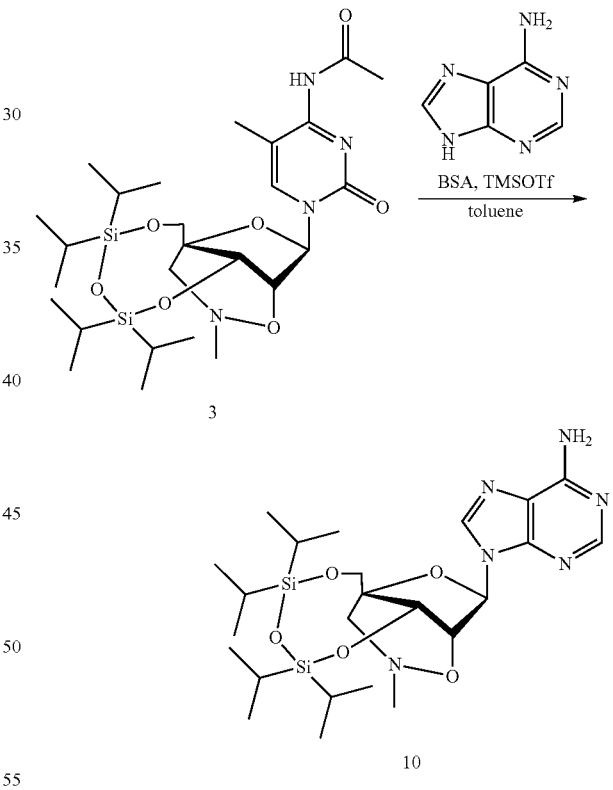

Adenine (202 mg, 1.5 mmol) was suspended in toluene (5.0 ml), and to the obtained suspension were added BSA (1.1 ml, 4.5 mmol) and TMSOTf (26 μL, 0.14 mmol). The obtained suspension was stirred at 100° C. until it became transparent. To the solution after stirring were added compound 3 (290 mg, 0.5 mmol) and TMSOTf (90 μL, 0.5 mmol), and the obtained solution was refluxed for 1.5 hr. The solution after refluxing was cooled to room temperature, and the solution was poured into saturated aqueous sodium hydrogen carbonate solution (30 ml). To the obtained solution was added ethyl acetate (30 ml), and the obtained solution was separated to give an ethyl acetate layer. The obtained ethyl acetate layer was washed with saturated aqueous sodium hydrogen carbonate solution. To the ethyl acetate layer after washing was added sodium sulfate, and the mixture was concentrated under reduced pressure to give a residue. The obtained residue was purified by silica gel column chromatography (hexane:ethyl acetate=50:50-0:100, v/v) to give compound 10 (192 mg, 70%) as a white solid.

Example 18

Synthesis of BNA$^{NC}$-2-amino-6-chloropurine nucleoside

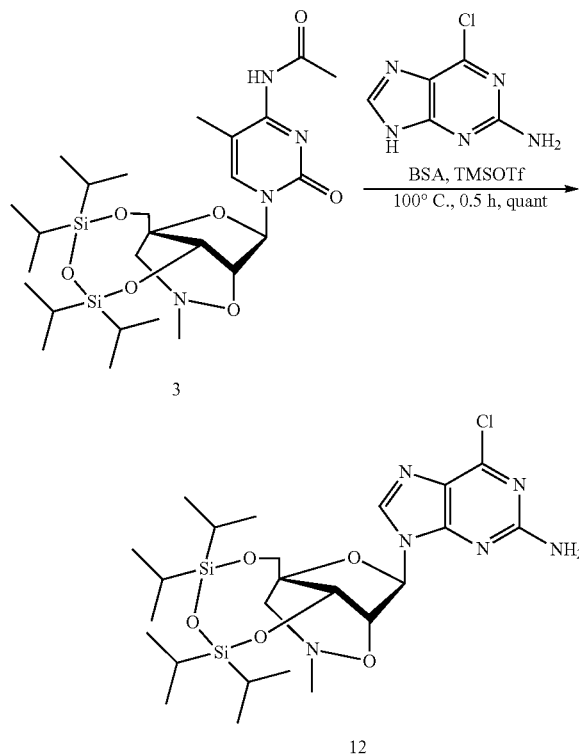

2-Amino-6-chloropurine (254 mg, 1.5 mmol) and compound 3 (290 mg, 0.5 mmol) were suspended in toluene (5 ml). To the obtained suspension was added BSA, and the obtained suspension was stirred at 100° C. for 30 min. To the solution after stirring was added TMSOTf (118 µL, 0.65 mmol), and the obtained solution was stirred at 100° C. for 30 min. The solution after stirring was poured into saturated aqueous sodium hydrogen carbonate solution (30 ml). To the obtained solution was added ethyl acetate (40 ml), the obtained solution was filtered through celite, and the filtrate was recovered. The recovered filtrate was separated to give an organic layer. The obtained organic layer was washed with saturated aqueous sodium hydrogen carbonate solution (30 ml), water (30 ml) and 1M hydrochloric acid (30 ml). To the organic layer after washing was added sodium sulfate, the obtained solution was concentrated to dryness under reduced pressure to give compound 12 (290 mg, 99%) as a pale-yellow solid.

$^1$H NMR (300 MHz, CDCl$_3$) δ 0.86-1.19 (m, 28H), 2.66 (d, J=11.14 Hz, 1H), 2.82 (s, 3H), 2.99 (d, J=11.14 Hz, 1H), 3.71 (d, J=12.84 Hz, 1H), 4.04 (d, J=12.84 Hz, 1H), 4.29 (d, J=3.21 Hz, 1H), 4.52 (d, J=3.02 Hz, 1H), 5.50 (br.s, 2H), 6.57 (s, 1H), 8.14 (s, 1H)

Example 19

Synthesis of BNA$^{NC}$-Adenosine Nucleoside

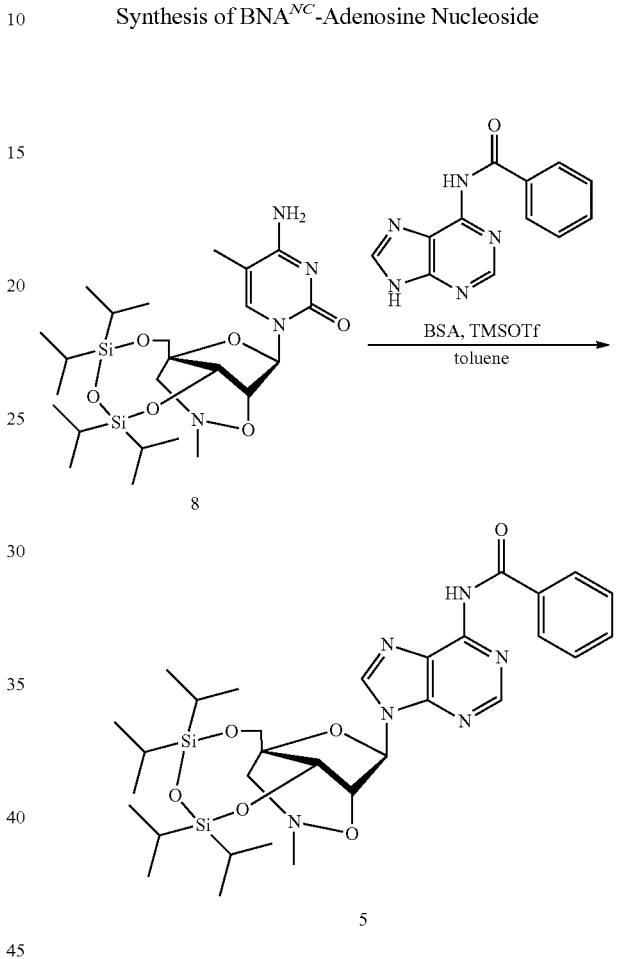

Compound 8 (270 mg, 0.5 mmol) and 6-N-benzoyladenine (359 mg, 1.5 mmol) were suspended in toluene (5 ml), and to the obtained suspension was added BSA (1.1 ml, 4.5 mmol). The obtained suspension was refluxed at 100° C. until it became transparent. To the solution after refluxing was added TMSOTf (118 µL, 0.65 mmol), and the obtained solution was stirred at 100° C. for 1 hr. The solution after stirring was poured into saturated aqueous sodium hydrogen carbonate solution (40 ml). To the obtained solution was added ethyl acetate (30 ml), and the obtained solution was filtrated, and the filtrate was recovered. The recovered filtrate was separated, and the obtained organic layer was washed with saturated aqueous sodium hydrogen carbonate solution (30 ml), and to the organic layer after washing was added anhydrous sodium sulfate. The obtained solution was concentrated under reduced pressure to give a residue. The obtained residue was purified by silica gel column chromatography (hexane:ethyl acetate=50:50, v/v) to give compound 5 (90 mg, 27%) as a white foamy solid.

Example 20

Synthesis of BNA$^{NC}$-Guanosine Nucleoside

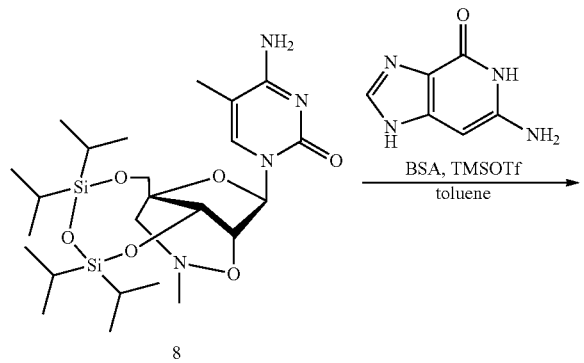

8

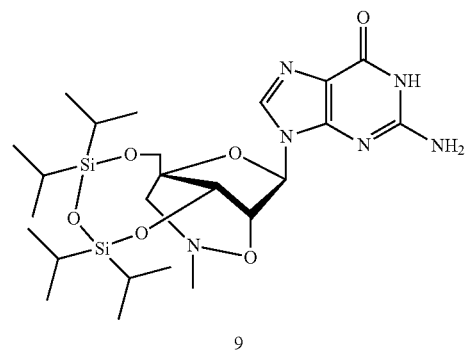

9

Guanine (227 mg, 1.5 mmol) was suspended in toluene (5 ml), and to the obtained suspension were added BSA (1.1 ml, 4.5 mmol) and TMSOTf (26 μL, 0.15 mmol). The obtained suspension was stirred at 100° C. until it became transparent. To the solution after stirring were added compound 8 (270 mg, 0.5 mmol) and TMSOTf (90 μL, 0.5 mmol), and the obtained solution was stirred at 100° C. for 1 hr. The solution after stirring was cooled to room temperature, the obtained solution was poured into saturated aqueous sodium hydrogen carbonate solution (30 ml). To the obtained solution was added ethyl acetate (30 ml), and the obtained solution was filtrated, and the filtrate was recovered. The recovered filtrate was separated to give an organic layer. The obtained organic layer was washed twice with saturated aqueous sodium hydrogen carbonate solution. To the organic layer after washing was added sodium sulfate. The obtained solution was concentrated under reduced pressure to give a residue. The obtained residue was purified by silica gel column chromatography (ethyl acetate:methanol=10:0-7:3, v/v). The objective fraction was concentrated under reduced pressure for dryness to give compound 9 (139 mg, 25%) as a white solid.

Example 21

Synthesis of BNA$^{NC}$-Adenosine Nucleoside

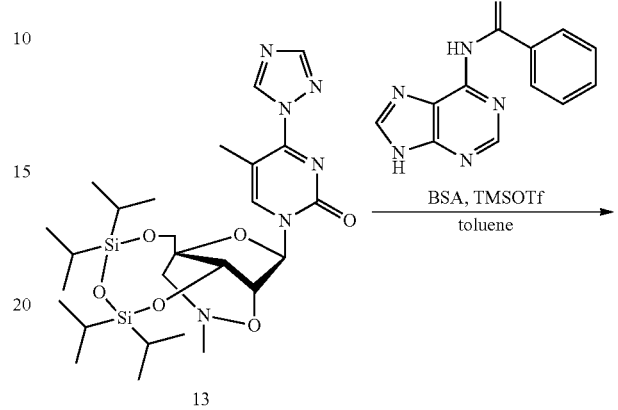

13

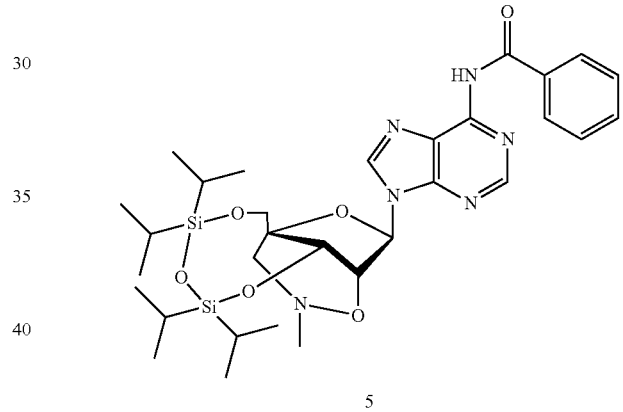

5

Compound 13 (55 mg, 0.093 mmol) and 6-N-benzoyladenine (40 mg, 0.17 mmol) were suspended in toluene (1.0 ml), and to the obtained suspension was added BSA (200 μL, 0.82 mmol). The obtained suspension was refluxed until it became transparent. The solution after refluxing was cooled until refluxing ceased. To the solution after cooling was added TMSOTf (20 μL, 0.82 mmol), and the obtained solution was refluxed for 30 min. The solution after refluxing was cooled to room temperature, and to the obtained solution was added saturated aqueous sodium hydrogen carbonate solution (10 ml). To the obtained solution was added ethyl acetate (30 ml), and the obtained solution was separated to give an organic layer. The obtained organic layer was washed with saturated aqueous sodium hydrogen carbonate solution (30 ml). To the organic layer after washing was added sodium sulfate, and the obtained solution was concentrated under reduced pressure to give a residue. The obtained residue was purified by silica gel column chromatography (hexane:ethyl acetate=6:4-4:6, v/v) to give compound 5 (51 mg, 84%) as a white foamy solid.

Example 22

Synthesis of BNA$^{NC}$-Guanosine Nucleoside

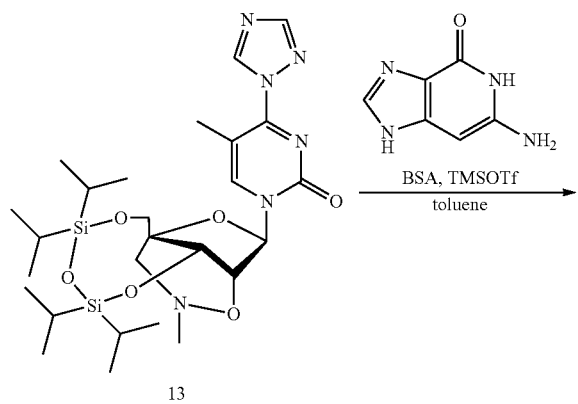

Guanine (25.3 mg, 0.17 mmol) was suspended in toluene (1 ml), and to the obtained suspension were added BSA (200 μL, 0.81 mmol) and TMSOTf (20 μl, 0.11 mmol). The obtained suspension was refluxed until it became transparent. The solution after refluxing was cooled to 100° C., to the solution was added compound 13 (50 mg, 0.084 mmol), and the mixture was stirred for 1 hr. The solution after stirring was poured into a mixed solution (130 ml) of pyridine-toluene-water-triethylamine (10:10:5:1, v/v/v/v). The obtained solution was stirred for 30 min. To the solution after stirring was added silica gel (5 g), and the solvent of the obtained solution was evaporated under reduced pressure to give a residue. The obtained residue was co-evaporated with toluene (5 ml, twice) to give a residue. The obtained residue was purified by silica gel column chromatography (ethyl acetate:methanol=90:10, v/v), and the objective fraction was concentrated to dryness under reduced pressure to give a white solid. To the obtained solid was added distilled water (50 ml), and the precipitate in the obtained solution was recovered by filtration. The obtained precipitate was washed with ethanol (2 ml). The precipitate after washing was drying by heating under reduced pressure to give compound 9 (17.6 mg, 37%) as a white solid.

Reference Example 1

Synthesis of 2-N-acetylguanosine BNA$^{NC}$ monomer unit

Synthesis of 2-N-acetylBNA$^{NC}$-guanosine derivative

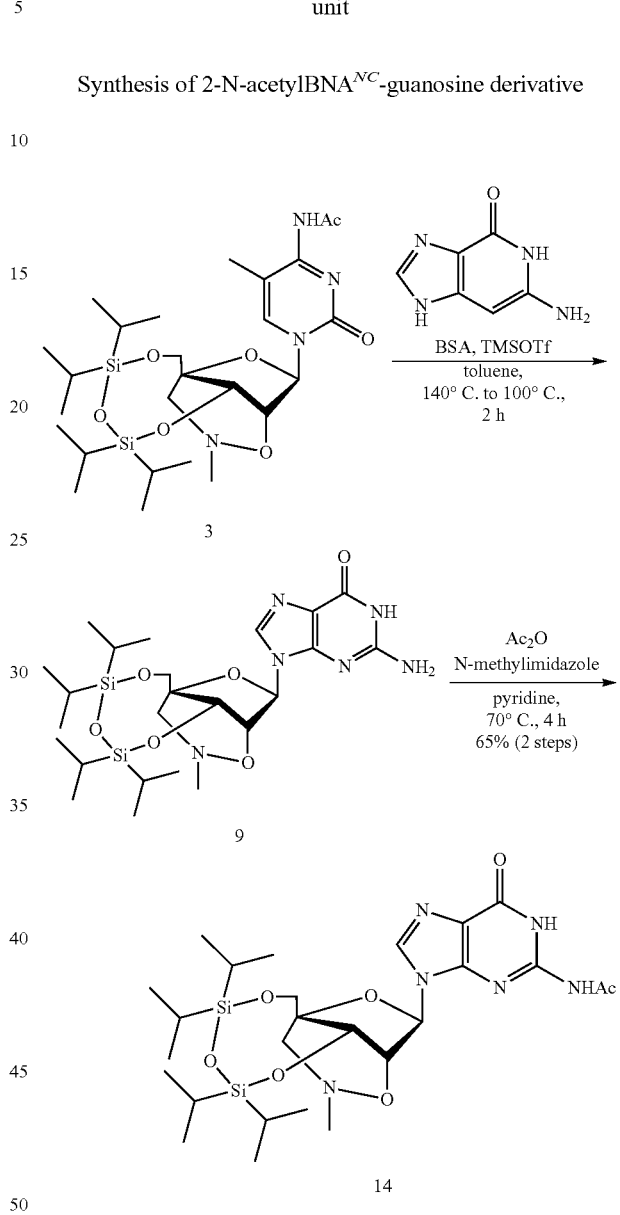

Guanine (775 mg, 5.13 mmol) was suspended in BSA (10 ml, 40.9 mmol) and toluene (10 ml), and the obtained suspension was heated to 140° C., and then refluxed for 1 hr. To the aforementioned suspension was added TMSOTf (60 μl, 0.33 mmol), and the obtained suspension was refluxed until it became transparent. The solution after refluxing was cooled to 100° C. (the temperature of oil bath), compound 3 (1.0 g, 1.71 mmol) and TMSOTf (300 μl, 1.65 mmol) were added thereto, and the obtained solution was reacted for 30 min. The obtained reaction mixture was poured into a mixed solution (130 ml) of pyridine-methanol-water-triethylamine (100:10:20:1, v/v/v/v). The obtained suspension was stirred at room temperature for 30 min. The suspension after stirring was concentrated to dryness, and co-evaporated (three times) with dry pyridine to give a residue. To the obtained residue were added dry pyridine (30 ml), acetic anhydride (20 ml) and N-methylimidazole (50 μl), and the reaction mixture was stirred with heating at 70° C. for 4 hr. The reaction mixture was cooled to room temperature, water (100 ml) was added thereto, and the mixture was stirred for 30 min. To the solution after stirring was added 25% aqueous ammonia (30 ml), and the mixture was stirred for 15 min. The obtained solution was concentrated under reduced pressure to give a residue. To the residue was added ethyl acetate (200 ml), and the obtained solution was washed with saturated brine-water (1:1, v/v). The obtained solution was separated to give an organic layer. The obtained organic layer was concentrated, and the residue was purified by silica gel column chromatography (hexane:ethyl acetate=85:15, v/v) to give compound 14 (680 mg, 65% (2 steps)).

$^1$H NMR (300 MHz, CDCl$_3$) δ 0.83-1.19 (m, 28H), 2.30 (s, 3H), 2.65 (d, J=11.14 Hz, 1H), 2.76 (s, 3H), 2.96 (d, J=11.14 Hz, 1H), 3.71 (d, J=12.84 Hz, 1H), 3.95-4.19 (m, 1H), 4.21-4.42 (m, 2H), 6.47 (s, 1H), 7.27 (s, 1H), 8.05 (s, 1H), 8.92 (br.s., 1H)

Synthesis of 2-N-acetyl-5'-O-(4,4'-dimethoxytrityl)-BNA$^{NC}$

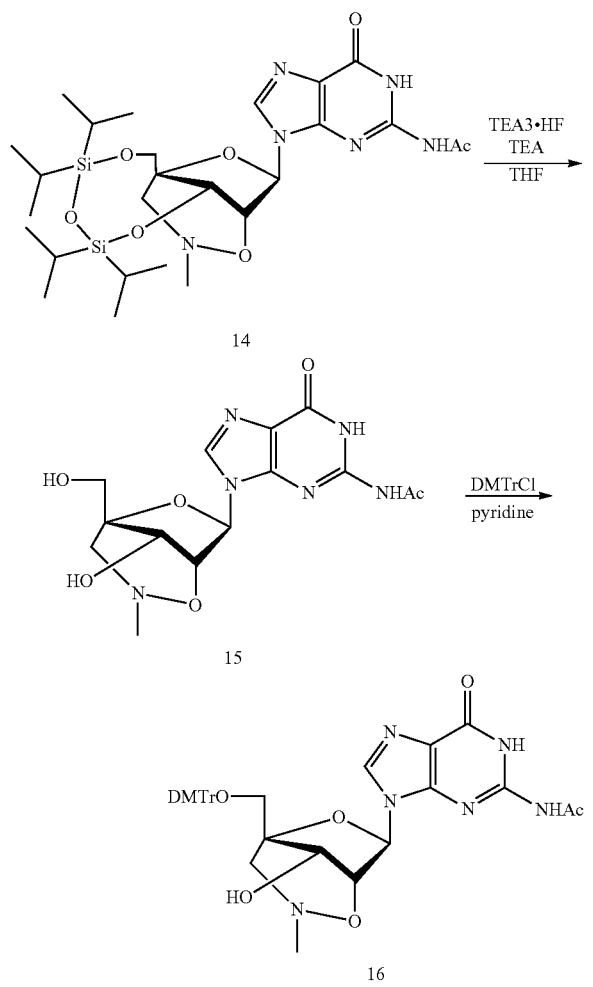

Compound 14 (1.5 g, 2.5 mmol) was dissolved in THF (25 ml), and triethylamine (700 μL, 5 mmol) and TEA·3HF (tri- ethylamine trihydrofluoride, 410 μL, 2.5 mmol) were added thereto, and the mixture was stirred at 50° C. for 2 hr. After stirring, THF was evaporated under reduced pressure, and diisopropyl ether (50 ml) was added thereto to precipitated compound 15. Compound 15 was collected by filtration. The obtained compound 15 was dried by co-evaporating with dry pyridine, and dissolved in pyridine (10 ml). DMTr-Cl (4,4'-dimethoxytrityl chloride, 1.3 g, 3.75 mmol) was added thereto, and the mixture was stirred overnight at room temperature. To the reaction mixture was added water (20 ml) to quench the reaction. The objective substance was extracted with ethyl acetate (200 ml). The ethyl acetate layer was washed successively with water (100 ml), saturated sodium hydrogen carbonate (100 ml) and saturated brine (100 ml), and concentrated. The residue was purified by DIOL-silica gel column chromatography (hexane:ethyl acetate=1:9, v/v) to give compound 16 (1 g, yield 60%, 2 step).

Compound 15

$^1$H NMR (300 MHz, DMSO-d$_6$) δ 2.14-2.21 (m, 3H), 2.55 (d, J=7.18 Hz, 2H), 2.66 (s, 3H), 2.80 (s, 2H), 3.50-3.72 (m, 3H), 4.02 (br.s., 1H), 4.34 (d, J=3.02 Hz, 1H), 5.14 (br.s., 1H), 5.45 (br.s., 1H), 6.40 (s, 1H), 8.14 (s, 1H)

Compound 16

$^1$H NMR (300 MHz, CDCl$_3$) δ 2.24 (s, 3H), 2.74 (s, 3H), 2.85 (d, J=11.90 Hz, 1H), 3.04 (d, J=11.90 Hz, 1H), 3.27-3.46 (m, 4H), 3.77 (s, 9H), 4.35 (br.s., 1H), 4.51 (d, J=2.83 Hz, 1H), 6.53 (s, 1H), 6.72-6.88 (m, 4H), 7.10-7.52 (m, 9H), 7.91 (s, 1H), 8.95 (br.s., 1H), 11.95 (br.s., 1H)

Amiditation Reaction

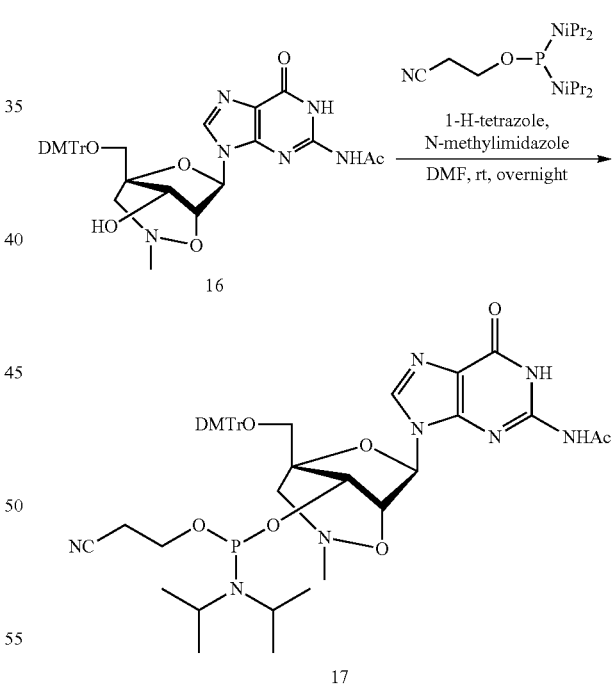

Compound 16 (870 mg, 1.3 mmol) was dried by co-evaporating (three times) with dry acetonitrile, and dissolved in DMF (9 ml). N,N,N',N'-Tetraisopropyl-2-cyanoethylphosphorodiamidite (784 mg, 2.6 mmol) and N-methylimidazole (51.8 μL, 0.65 mmol) were added thereto, and then tetrazole (91 mg, 1.3 mmol) was added thereto, and the mixture was stirred overnight at room temperature. The reaction mixture was diluted with ethyl acetate (40 ml), and washed twice with saturated brine (40 ml). The organic layer was dried over anhydrous sodium sulfate, and concentrated. The residue was purified by DIOL-silica gel column chromatography (0.5% triethylamine containing-hexane-ethyl acetate) to give compound 17 (1.0 g, 1.15 mmol, 88%) as a white foamy solid.

$^1$H NMR (300 MHz, CDCl$_3$) δ 0.97-1.30 (m, 14H), 2.22 (2s, 3H), 2.34-2.38 (m, 2H), 2.73, 2.75 (2s, 3H), 2.83-2.88 (m, 1H), 3.01-3.11 (m, 1H), 3.27-3.80 (m, 8H), 4.46, 4.10 (2dd, 1H, J1=8.03 Hz, J2=3.12 Hz), 4.67, 4.80 (2d, 1H, J=2.83 Hz), 6.52, 6.55 (2s, 1H) 6.80-6.83 (m, 4H), 7.21-7.66 (m, 9H), 7.97, 7.98 (2s, 1H), 8.82 (br.s, 1H), 11.96 (br.s, 1H).

$^{31}$P NMR (121 MHz) δ 150.71, 151.03

Reference Example 2

Synthesis step of BNA$^{NC}$ monomer unit from purine nucleoside wherein substituent B' is
i) 6-O-diphenylcarbamoyl-2-N-acetylguanin-9-yl group
or
ii) 6-N-benzoyladenin-9-yl group

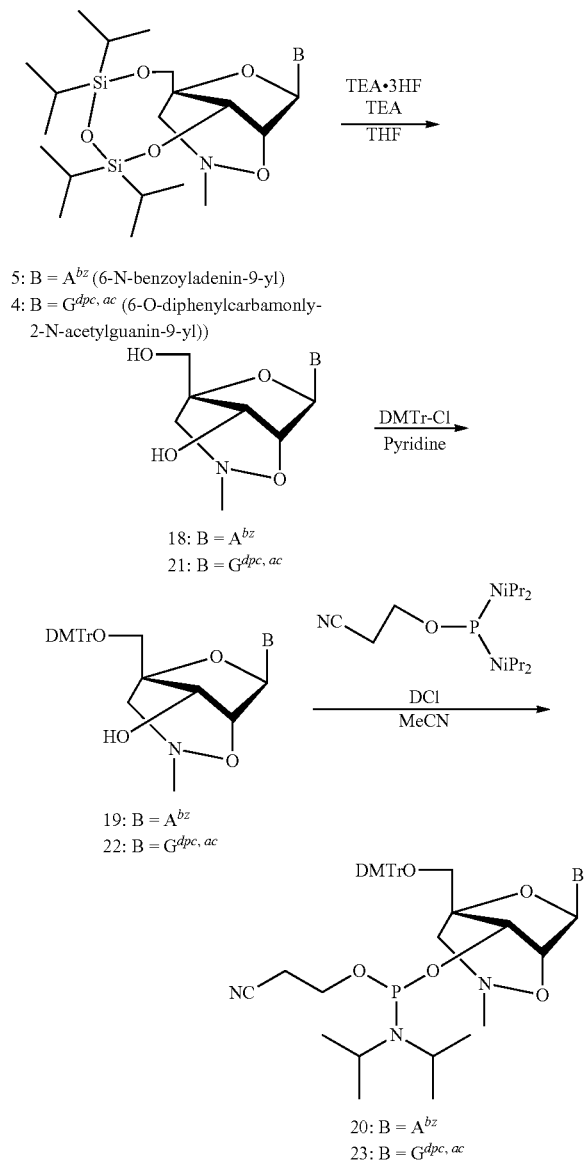

5: B = A$^{bz}$ (6-N-benzoyladenin-9-yl)
4: B = G$^{dpc, ac}$ (6-O-diphenylcarbamonly-2-N-acetylguanin-9-yl))

18: B = A$^{bz}$
21: B = G$^{dpc, ac}$

19: B = A$^{bz}$
22: B = G$^{dpc, ac}$

20: B = A$^{bz}$
23: B = G$^{dpc, ac}$ i) Synthesis of 6-N-benzoyladenosine BNA$^{NC}$ Monomer Compound 5 (530 mg, 0.81 mmol) was dissolved in THF (10 ml), and triethylamine (200 μL, 1.42 mmol) and triethylamine trihydrofluoride (460 μL, 2.84 mmol) were added thereto, and the mixture was stirred for 1.5 hr at room temperature. The reaction mixture was concentrated, diluted with ethyl acetate (10 ml), and purified by silica gel column chromatography (ethyl acetate-methanol) to give compound 18 (330 mg).

$^1$H NMR (300 MHz, DMSO-d$_6$) δ 2.72 (s, 3H), 2.86 (s, 2H), 3.62 (m, 2H), 4.18 (dd, J=5.5 Hz, 3.2 Hz, 1H), 4.52 (d, J=3.0 Hz, 1H), 5.12 (t, J=5.9 Hz, 1H), 5.47 (d, J=5.5 Hz, 1H), 6.67 (s, 1H), 7.48-7.72 (m, 3H), 8.01-8.09 (m, 2H), 8.60 (s, 1H), 8.75 (s, 1H), 11.22 (br.s, 1H).

Compound 18 (300 mg, 0.72 mmol) was dried by co-evaporating with dry pyridine, and dissolved in pyridine (4 ml). 4,4'-Dimethoxytrityl chloride (271 mg, 0.8 mmol) was added thereto, and the mixture was stirred at room temperature for 12 hr. To the reaction mixture was added saturated aqueous sodium hydrogen carbonate solution (10 ml), and the aqueous layer was extracted with ethyl acetate (25 ml). The obtained organic layer was washed with saturated aqueous sodium hydrogen carbonate solution (10 ml), and dried over anhydrous sodium sulfate, and concentrated. The residue was purified by silica gel column chromatography (hexane-ethyl acetate) to give compound 19 (416 mg, 0.58 mmol).

$^1$H NMR (300 MHz, CDCl$_3$) δ 2.78 (s, 3H), 2.82-3.11 (m, 3H), 3.38 (s, 2H), 3.77 (s, 6H), 4.39 (br.s, 1H), 4.67 (d, J=2.8 Hz, 1H), 6.75-6.89 (m, 5H), 7.15-7.64 (m, 12H), 8.00 (d, 2H), 8.33 (s, 1H), 8.79 (s, 1H), 9.17 (br.s, 1H).

Compound 19 (410 mg, 0.57 mmol) was dried by co-evaporating (twice) with anhydrous acetonitrile, and dissolved in anhydrous acetonitrile (2.5 ml). N,N,N',N'-Tetraisopropyl-2-cyanoethylphosphorodiamidite (200 μL, 0.63 mmol) and 4,5-dicyanoimidazole (DCI, 71 mg, 0.6 mmol) were successively added thereto. The mixture was stirred at room temperature for 2 hr, and the reaction mixture was diluted with ethyl acetate (20 ml). Saturated aqueous sodium hydrogen carbonate solution (10 ml) was added thereto to quench the reaction. The organic layer was washed with saturated aqueous sodium hydrogen carbonate solution (10 ml), dried over anhydrous sodium sulfate, and concentrated. The residue was purified by silica gel column chromatography (Diol-silica gel (manufactured by Fuji Silysia, hexane-acetone) to give the objective BNA$^{NC}$-adenosine monomer (compound 20: 480 mg, 0.52 mmol).

$^1$H NMR (300 MHz, CDCl$_3$) δ 0.92-1.22 (m, 12H), 2.26-2.48 (m, 2H), 2.76, 2.78 (2s, 3H), 2.82-2.95 (m, 2H), 3.27-3.64 (m, 4H), 3.78-3.79 (m, 6H), 4.095, 4.48 (2dd, 1H, J1=8.03 Hz, 3.12 Hz, J2=7.18 Hz, 3.02 Hz), 4.67, 4.80 (2d, 1H, J=2.83 Hz, J=2.83 Hz), 6.52, 6.55 (2s, 1H), 6.80-6.83 (m, 2H), 7.21-7.36 (m, 9H), 7.43-7.46 (m, 2H), 8.35, 8.42 (2s, 1H), 8.84 (s, 1H), 9.05 (br.s, 1H).

$^{31}$P NMR (121 MHz) δ 149.08, 149.36 ii) Synthesis of 2-N-acetyl-6-O-diphenylcarbamoyl-BNA$^{NC}$-guanosine monomer unit Compound 4 (320 mg, 0.4 mmol) was dissolved in THF (5 ml), and triethylamine (98 μL, 0.7 mmol) and triethylamine trihydrofluoride (228 μL, 1.4 mmol) were added thereto, and the mixture was stirred at room temperature for 1.5 hr. The reaction mixture was concentrated, and the residue was diluted with ethyl acetate (10 ml), and the mixture was purified by silica gel column chromatography (ethyl acetate-methanol) to give compound 21 (180 mg, 0.32 mmol).

¹H NMR (300 MHz, CDCl₃) δ 2.38 (s, 3H), 2.59-2.92 (m, 4H), 3.68 (s, 2H), 3.91 (br.s, 1H), 4.21 (br.s, 1H), 4.48 (d, J=2.64 Hz, 1H), 4.58 (br.s, 1H), 6.57 (s, 1H), 7.11-7.54 (m, 10H), 8.25 (s, 1H), 8.92 (s, 1H)

Compound 21 (160 mg, 0.28 mmol) was dried by co-evaporating with dry pyridine, and dissolved in pyridine (1.5 ml). 4,4'-Dimethoxytrityl chloride (108 mg, 0.32 mmol) was added thereto, and the mixture was stirred at room temperature for 12 hr. To the reaction mixture was added saturated aqueous sodium hydrogen carbonate solution (10 ml), and the aqueous layer was extracted with ethyl acetate (20 ml). The obtained organic layer was washed with saturated aqueous sodium hydrogen carbonate solution (10 ml), and dried over anhydrous sodium sulfate, and concentrated. The residue was purified by silica gel column chromatography (hexane-ethyl acetate) to give compound 22 (176 mg, 0.20 mmol).

¹H NMR (300 MHz, CDCl₃) δ2.49 (s, 3H), 2.72 (d, J=8.50 Hz, 1H), 2.78 (s, 3H), 2.85 (d, J=11.90 Hz, 1H), 3.04 (d, J=11.90 Hz, 1H), 3.35 (s, 2H), 3.75 (m, 6H), 4.47 (br, 1H), 4.70 (d, J=2.83 Hz, 1H), 6.67 (s, 1H), 6.80 (d, J=8.69 Hz, 4H), 7.14-7.52 (m, 19H), 8.15 (s, 1H), 8.22 (s, 1H)

Compound 22 (140 mg, 0.16 mmol) was dried by co-evaporating (twice) with anhydrous acetonitrile, and dissolved in anhydrous acetonitrile (1 ml). N,N,N',N'-Tetraisopropyl-2-cyanoethylphosphorodiamidite (76 μL, 0.24 mmol) and 4,5-dicyanoimidazole (21 mg, 0.18 mmol) were successively added thereto. The mixture was stirred at room temperature for 2 hr, and N,N,N',N'-tetraisopropyl-2-cyanoethylphosphorodiamidite (38 μL, 0.12 mmol) and 4,5-dicyanoimidazole (10 mg, 0.09 mmol) were successively added thereto. The mixture was stirred at room temperature for 1 hr, the reaction mixture was diluted with ethyl acetate (10 ml), and saturated aqueous sodium hydrogen carbonate solution (5 ml) was added thereto to quench the reaction. The organic layer was washed with saturated aqueous sodium hydrogen carbonate solution (10 ml), dried over anhydrous sodium sulfate, and concentrated. The residue was purified by silica gel column chromatography (Diol-silica gel (manufactured by Fuji Silysia, hexane-acetone) to give the objective BNA$^{NC}$-guanosine monomer (compound 23: 153 mg, 0.14 mmol).

¹H NMR (300 MHz, CDCl₃) δ 0.92-1.19 (m, 12H), 2.27-2.49 (m, 2H), 2.58 (s, 3H), 2.74, 2.77 (2s, 3H), 2.82-3.06 (m, 2H), 3.27-3.73 (m, 4H), 3.77-3.78 (m, 6H), 4.20-4.45 (m, 1H), 4.73 (m, 1H), 6.68 (2s, 1H), 6.77-6.87 (m, 4H), 7.20-7.51 (m, 19H), 7.98 (s, 1H), 8.27, 8.31 (2s, 1H)

³¹P NMR (121 MHz) δ 148.72, 149.41

Reference Example 3

Synthesis of 3-N-benzoylthymidine derivative

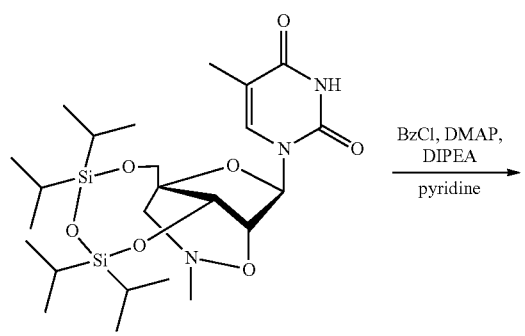

7

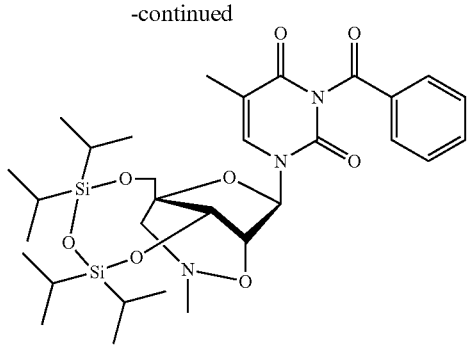

6

Compound 7 (3.0 g, 5.54 mmol) was dissolved in pyridine (30 ml), isopropyldiethylamine (1.93 ml, 11.1 mmol, 2.0 eq), benzoyl chloride (0.84 ml, 7.20 mmol, 1.3 eq) and dimethylaminopyridine (68 mg, 0.55 mmol, 0.1 eq) were added thereto. The mixture was stirred at 60° C. for 1 hr, and distilled water was added thereto to quench the reaction. The reaction mixture was concentrated under reduced pressure, and the residue was diluted with ethyl acetate (30 ml). The mixture was washed twice with saturated aqueous sodium hydrogen carbonate solution (containing NaCl), the organic layer was dried over magnesium sulfate, and the solvent was evaporated under reduced pressure. The residue was purified by silica gel column chromatography (hexane:ethyl acetate=8:2-5:5, v/v) to give compound 6 as a foamy solid (3.5 g, 5.42 mmol, 98%).

¹H NMR (300 MHz, CDCl₃) δ 0.96-1.18 (28H, m), 1.97 (3H, d, J=0.9 Hz), 2.59 (1H, d, J=11.1 Hz), 2.70 (3H, s), 2.91 (1H, d, J=11.1 Hz), 3.69 (1H, d, J=13.0 Hz), 3.99 (1H, d, J=3.0 Hz), 4.06 (1H, d, J=13.0 Hz), 4.36 (1H, d, J=3.0 Hz), 6.27 (1H, s), 7.41-7.55 (2H, m), 7.58-7.71 (1H, m), 7.82 (1H, d, J=1.1 Hz), 7.85-7.96 (2H, m).

Reference Example 4

Synthesis of Compound 13

Synthesis of Triazole Derivative

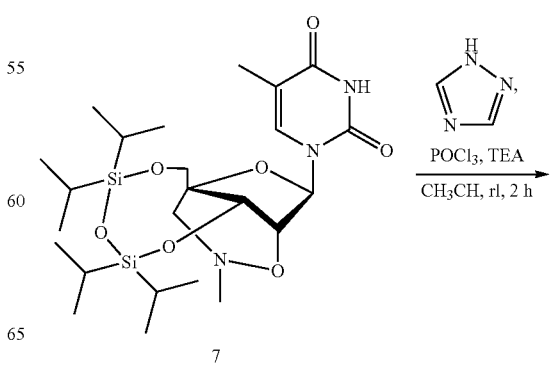

7

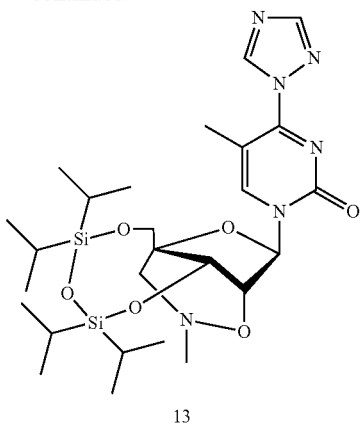

13

Compound 7 (3.2 mmol, 1.8 g) was dissolved in acetonitrile (20 ml), triethylamine (38 mmol, 5.4 ml), 1,2,4-triazole (26 mmol, 1.8 g) and phosphorus oxychloride (6.4 mmol, 0.59 ml) were added thereto, and the reaction mixture was stirred at room temperature for 2 hr. To the reaction mixture was added ice to quench the reaction, and the mixture was partitioned between ethyl acetate and water. The separated organic layer was washed with saturated brine, and dried over sodium sulfate. The sodium sulfate was filtered off, and the organic layer was concentrated. The obtained residue was purified by silica gel column chromatography (hexane/ethyl acetate=30:70-0:100, v/v) to give compound 13 (1.8 g, 94%) as a white foamy substance.

$^1$H NMR (300 MHz, CDCl$_3$) δ 1.13-0.94 (m, 28H), 2.48 (s, 3H), 2.65 (d, 1H, J=11.1 Hz), 2.79 (s, 3H), 2.96 (d, 1H, J=11.1 Hz), 3.71 (d, 1H, J=13.0 Hz), 3.92 (d, 1H, J=3.0 Hz), 4.98 (d, 1H, J=12.7 Hz), 4.52 (d, 1H, J=3.0 Hz), 6.39 (s, 1H), 8.12 (s, 1H), 8.35 (s, 1H), 9.31 (s, 1H)

The compound names of the aforementioned compounds 1 to 23 described in Examples and Reference Examples are shown in the following.

TABLE 1

| | Compound name |
|---|---|
| Compound 1 | 4-N-acetyl-3'-O-benzyl-5'-O-methanesulfonyl-5-methyl-2'-O,4'-C-(N-methylaminomethylene)cytidine |
| Compound 2 | 6-N-benzoyl-3'-O-benzyl-5'-O-methanesulfonyl-2'-O,4'-C-(N-methylaminomethylene)adenosine |
| Compound 3 | 4-N-acetyl-3',5'-O-(tetraisopropyldisiloxane)-5-methyl-2'-O,4'-C-(N-methylaminomethylene)cytidine |
| Compound 4 | 2-N-acetyl-3',5'-O-(tetraisopropyldisiloxane)-2'-O,4'-C-(N-methylaminomethylene)-6-O-diphenylcarbamoylguanosine |
| Compound 5 | 6-N-benzoyl-3',5'-O-(tetraisopropyldisiloxane)-2'-O,4'-C-(N-methylaminomethylene)adenosine |
| Compound 6 | 3-N-benzoyl-3',5'-O-(tetraisopropyldisiloxane)-4-methyl-2'-O,4'-C-(N-methylaminomethylene)uridine |
| Compound 7 | 3',5'-O-(tetraisopropyldisiloxane)-5-methyl-2'-O,4'-C-(N-methylaminomethylene)uridine |
| Compound 8 | 3',5'-O-(tetraisopropyldisiloxane)-5-methyl-2'-O,4'-C-(N-methylaminomethylene)cytidine |
| Compound 9 | 3',5'-O-(tetraisopropyldisiloxane)-2'-O,4'-C-(N-methylaminomethylene)guanosine |
| Compound 10 | 3',5'-O-(tetraisopropyldisiloxane)-2'-O,4'-C-(N-methylaminomethylene)adenosine |
| Compound 11 | 6-N-acetyl-3',5'-O-(tetraisopropyldisiloxane)-2'-O,4'-C-(N-methylaminomethylene)adenosine |
| Compound 12 | 2-amino-6-chloro-9-[3',5'-O-(tetraisopropyldisiloxane)-2'-O,4'-C-(N-methylaminomethylene)-β-D-ribofuranosyl]purine |

TABLE 1-continued

| | Compound name |
|---|---|
| Compound 13 | 1-[3',5'-O-(tetraisopropyldisiloxane)-2'-O,4'-C-(N-methylaminomethylene)-β-D-ribofuranosyl]-5-methyl-4-(1,2,3-triazol-1-yl)pyrimidin-2-one |
| Compound 14 | 2-N-acetyl-3',5'-O-(tetraisopropyldisiloxane)-2'-O,4'-C-(N-methylaminomethylene)guanosine |
| Compound 15 | 2-N-acetyl-2'-O,4'-C-(N-methylaminomethylene)guanosine |
| Compound 16 | 2-N-acetyl-5'-O-(4,4'-dimethoxytriphenyl)methyl-2'-O,4'-C-(N-methylaminomethylene)guanosine |
| Compound 17 | 2-N-acetyl-3'-O-[2-cyanoethoxy(diisopropylamino)phosphino]-5'-O-(4,4'-dimethoxytriphenyl)methyl-2'-O,4'-C-(N-methylaminomethylene)guanosine |
| Compound 18 | 6-N-benzoyl-2'-O,4'-C-(N-methylaminomethylene)-adenosine |
| Compound 19 | 6-N-benzoyl-5'-O-(4,4'-dimethoxytriphenyl)methyl-2'-O,4'-C-(N-methylaminomethylene)adenosine |
| Compound 20 | 6-N-benzoyl-3'-O-[2-cyanoethoxy(diisopropylamino)phosphino]-5'-O-(4,4'-dimethoxytriphenyl) methyl-2'-O,4'-C-(N-methylaminomethylene)adenosine |
| Compound 21 | 2-N-acetyl-2'-O,4'-C-(N-methylaminomethylene)-6-O-diphenylcarbamoylguanosine |
| Compound 22 | 2-N-acetyl-5'-O-(4,4'-dimethoxytriphenyl)methyl-2'-O,4'-C-(N-methylaminomethylene)-6-O-diphenylcarbamoylguanosine |
| Compound 23 | 2-N-acetyl-3'-O-[2-cyanoethoxy(diisopropylamino)phosphino]-5'-O-(4,4'-dimethoxytriphenyl)methyl-2'-O,4'-C-(N-methylaminomethylene)-6-O-diphenylcarbamoylguanosine |

INDUSTRIAL APPLICABILITY

According to the present invention, an NC type nucleoside having a purine nucleobase can be conveniently with ease produced. In addition, since the purine nucleobase moiety can be N9 position-selectively transglycosylated, an NC type nucleoside having a purine nucleobase can be regioselectively produced.

This application is based on patent application No. 2009-085897 filed in Japan, the contents of which are hereby incorporated by reference.

The invention claimed is:

1. A method of producing a purine nucleoside represented by the formula (I')

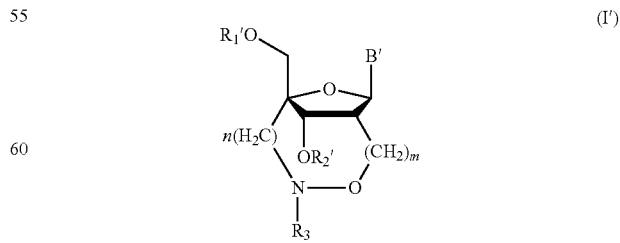

or a salt thereof, comprising reacting a pyrimidine nucleoside represented by the formula (I)

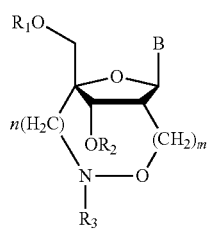

(I)

or a salt thereof with a purine nucleobase represented by the formula B'H in a solvent, in the presence of a Lewis acid:
wherein
$R_1$ and $R_1'$ are each independently a hydrogen atom, a hydroxy-protecting group, an alkyl group, an alkenyl group, a cycloalkyl group, an aryl group optionally having substituent(s), an aralkyl group optionally having substituent(s), an acyl group, an aliphatic or aromatic sulfonyl group, or a silyl group,
$R_2$ and $R_2'$ are each independently a hydrogen atom, a hydroxy-protecting group, an alkyl group, an alkenyl group, a cycloalkyl group, an aryl group optionally having substituent(s), an aralkyl group optionally having substituent(s), an acyl group, an aliphatic or aromatic sulfonyl group, or a silyl group, or
$R_1$ and $R_2$ in combination or $R_1'$ and $R_2'$ in combination optionally form a group represented by the formula

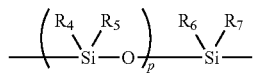

wherein
$R_4$ in the number of p, $R_5$ in the number of p, $R_6$, and $R_7$ are each independently an alkyl group or an aryl group, and
p is an integer of 1 to 3,
$R_3$ is a hydrogen atom, an alkyl group, an alkenyl group, a cycloalkyl group, an aryl group optionally having substituent(s), an aralkyl group optionally having substituent(s), an acyl group, or an aliphatic or aromatic sulfonyl group,
B is a residue derived from a pyrimidine nucleobase optionally having substituent(s),
B' is a residue derived from a purine nucleobase optionally having substituent(s),
m is an integer of 0 to 2, and
n is an integer of 1 to 3.

2. The method of claim 1, wherein B is a residue derived from a pyrimidine nucleobase optionally having substituent(s), and is bonded at the N1-position on the pyrimidine ring, and B' is a residue derived from a purine nucleobase optionally having substituent(s), and is bonded at the N9-position on the purine ring.

3. The method of claim 1 or 2, wherein B is a residue derived from a pyrimidine nucleobase protected by an amino-protecting group, and is bonded at the N1-position on the pyrimidine ring.

4. The method of claim 1 or 2, wherein B is a residue derived from a thymine nucleobase wherein the nitrogen atom at the N3-position is protected by a benzoyl group, which is bonded at the N1-position on the pyrimidine ring.

5. The method of claim 1 or 2, wherein B' is a residue derived from a purine nucleobase having a bulky substituent at the C6-position on the purine ring and optionally having additional substituent(s), and is bonded at the N9-position on the purine ring.

6. The method of claim 1 or 2 wherein B' is a residue derived from a purine nucleobase having an amino group optionally protected by a benzoyl group at the C6-position, and is bonded at the N9-position on the purine ring.

7. The method of claim 1 or 2, wherein B' is a residue derived from a purine nucleobase having a hydroxyl group optionally protected by a diphenyicarbamoyl group at the C6-position, and optionally having an amino group protected by an amino-protecting group, and is bonded at the N9-position on the purine ring.

8. The method of claim 1 or 2 wherein B' is a residue derived from a purine nucleobase having an oxo group at the C6-position, and optionally having an amino group protected by an amino-protecting group, and is bonded at the N9-position on the purine ring.

9. The method of claim 1 or 2 wherein the eaction is performed in the presence of a silylating agent.

10. The method of claim 1 or 2 wherein the reaction is performed at 80 to 120° C.

11. The method of claim 1 or 2 wherein the solvent is toluene.

12. The method of claim 1 or 2, wherein the reaction is performed by reacting the pyrimidine nucleoside represented by the formula (I)

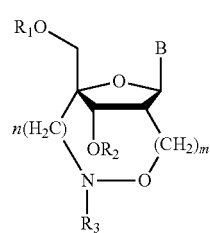

(I)

wherein each symbol is as defined in claim 1, or a salt thereof, with the purine nucleobase represented by the formula B'H wherein B' is as defined in claim 1, in the presence of the Lewis acid and a silylating agent, and then subjecting the resulting compound to a reaction for removal of a silyl group derived from the silylating agent.

13. The method of claim 1 or 2, wherein $R_1$ and $R_1'$ are each independently a hydrogen atom; an acyl group; an aliphatic or aromatic sulfonyl group; a methyl group substituted by 1 to 3 aryl groups; a methyl group substituted by 1 to 3 aryl groups optionally substituted by 1 to 3 substituents selected from the group consisting of alkyl, alkoxy, a halogen atom, and cyano; or a silyl group.

14. The method of claim 1 or 2, wherein $R_1$ and $R_1'$ are each independently a hydrogen atom, an acetyl group, a benzoyl group, a methanesulfonyl group, a p-toluenesulfonyl group, a benzyl group, a p-methoxybenzyl group, or a tert-butyldiphenylsilyl group.

15. The method of claim 1 or 2, wherein $R_2$ and $R_2'$ are each independently a hydrogen atom; an acyl group; an aliphatic or aromatic sulfonyl group; a methyl group substituted by 1 to 3 aryl groups; a methyl group substituted by 1 to 3 aryl groups optionally substituted by 1 to 3 substituents selected from the group consisting of alkyl, alkoxy, a halogen atom, and cyano; or a silyl group.

16. The method of claim 1 or 2, wherein $R_2$ and $R_2'$ are each independently a hydrogen atom, an acetyl group, a benzoyl group, a methanesulfonyl group, a p-toluenesulfonyl group, a benzyl group, a p-methoxybenzyl group, or a tert-butyldiphenylsilyl group.

17. The method of claim 1 or 2, wherein $R_1$ and $R_2$ in combination or $R_1'$ and $R_2'$ in combination form a group represented by the formula

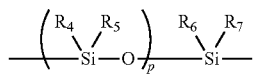

wherein $R_4$ in the number of p, $R_5$ in the number of p, $R_6$, and $R_7$ are each independently a $C_{1-6}$ alkyl group, and p is an integer of 1 to 3.

18. The method of claim 1 or 2, wherein $R_3$ is a hydrogen atom, an alkyl group, an alkenyl group, an aryl group, a methyl group substituted by 1 to 3 aryl groups, an aliphatic or aromatic sulfonyl group, or a phenoxyacetyl group.

19. The method of claim 1 or 2, wherein $R_3$ is a $C_{1-6}$ alkyl group.

20. The method of claims 1 or 2, wherein m is 0 and n is 1.

21. The method of claim 1 or 2,
wherein
B' is a residue derived from a purine nucleobase optionally having substituent(s), and is bonded at the N9-position on the purine ring.

22. A method of producing a purine nucleoside represented by the formula (I')

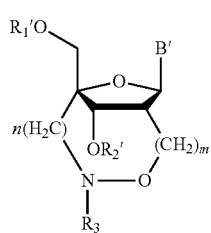

or a salt thereof, comprising reacting a pyrimidine nucleoside represented by the formula (I)

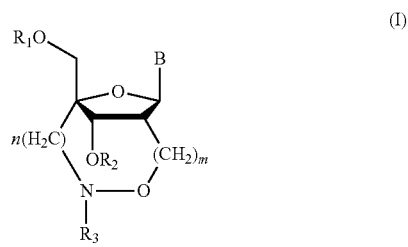

or a salt thereof with a purine nucleobase wherein the dissociative hydrogen atom is silylated, which is represented by the formula B'H, in a solvent, in the presence of a Lewis acid:
wherein $R_1$ and $R_1'$ are each independently a hydrogen atom, a hydroxy-protecting group, an alkyl group, an alkenyl group, a cycloalkyl group, an aryl group optionally having substituent(s), an aralkyl group optionally having substituent(s), an acyl group, an aliphatic or aromatic sulfonyl group, or a silyl group, $R_2$ and $R_2'$ are each independently a hydrogen atom, a hydroxy-protecting group, an alkyl group, an alkenyl group, a cycloalkyl group, an aryl group optionally having substituent(s), an aralkyl group optionally having substituent(s), an acyl group, an aliphatic or aromatic sulfonyl group, or a silyl group, or $R_1$ and $R_2$ in combination or $R_1'$ and $R_2'$ in combination optionally form a group represented by the formula

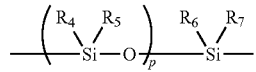

wherein $R_4$ in the number of p, $R_5$ in the number of p, $R_6$, and $R_7$ are each independently an alkyl group or an aryl group, and p is an integer of 1 to 3, $R_3$ is a hydrogen atom, an alkyl group, an alkenyl group, a cycloalkyl group, an aryl group optionally having substituent(s), an aralkyl group optionally having substituent(s), an acyl group, or an aliphatic or aromatic sulfonyl group, B' is a residue derived from a pyrimidine nucleobase optionally having substituent(s), B' is a residue derived from a purine nucleobase optionally having substituent(s), m is an integer of 0 to 2, and n is an integer of 1 to 3.

* * * * *

UNITED STATES PATENT AND TRADEMARK OFFICE
CERTIFICATE OF CORRECTION

| | |
|---|---|
| PATENT NO. | : 8,653,254 B2 |
| APPLICATION NO. | : 13/260096 |
| DATED | : February 18, 2014 |
| INVENTOR(S) | : Umemoto et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 217 days.

Signed and Sealed this
Twelfth Day of May, 2015

Michelle K. Lee
*Director of the United States Patent and Trademark Office*